(12) United States Patent
Mojarrad et al.

(10) Patent No.: US 12,318,593 B2
(45) Date of Patent: Jun. 3, 2025

(54) HYDRAULIC-PNEUMATIC PRESSURIZED CHAMBER DRUG DELIVERY SYSTEM

(71) Applicant: AMGEN INC., Thousand Oaks, CA (US)

(72) Inventors: Mehran Mojarrad, Thousand Oaks, CA (US); John K. Hoffman, Vista, CA (US); Paul Daniel Faucher, San Marcos, CA (US); Matthew Pacheco, Vista, CA (US); Ed Maher, Oceanside, CA (US)

(73) Assignee: AMGEN INC., Thousand Oaks, CA (US)

(*) Notice: Subject to any disclaimer, the term of this patent is extended or adjusted under 35 U.S.C. 154(b) by 897 days.

(21) Appl. No.: 16/630,329

(22) PCT Filed: Aug. 7, 2018

(86) PCT No.: PCT/US2018/045467
§ 371 (c)(1),
(2) Date: Jan. 10, 2020

(87) PCT Pub. No.: WO2019/032482
PCT Pub. Date: Feb. 14, 2019

(65) Prior Publication Data
US 2020/0164155 A1    May 28, 2020

Related U.S. Application Data

(60) Provisional application No. 62/543,058, filed on Aug. 9, 2017.

(51) Int. Cl.
*A61M 5/31*    (2006.01)
*A61M 5/19*    (2006.01)
(Continued)

(52) U.S. Cl.
CPC .......... *A61M 5/31576* (2013.01); *A61M 5/19* (2013.01); *A61M 5/3202* (2013.01); *A61M 5/3221* (2013.01); *A61M 5/343* (2013.01)

(58) Field of Classification Search
CPC .... A61M 2005/14513; A61M 5/14526; A61M 5/155; A61M 5/2053; A61M 5/2046
See application file for complete search history.

(56) References Cited

U.S. PATENT DOCUMENTS 4,031,889 A    6/1977  Pike
4,227,528 A *  10/1980  Wardlaw ............... A61M 5/283
                                                    604/139
(Continued)

FOREIGN PATENT DOCUMENTS

EP    600754 A2 *  6/1994  ........ A61M 5/14526
EP    1545661 A2    6/2005
(Continued)

OTHER PUBLICATIONS

Written Opinion of International Patent Application PCT/US2018/045467, dated Feb. 26, 2019.
(Continued)

*Primary Examiner* — William R Carpenter
(74) *Attorney, Agent, or Firm* — MARSHALL, GERSTEIN & BORUN LLP

(57) ABSTRACT

A wearable drug delivery device includes a housing, a needle assembly at least partially disposed in the housing, and a drive assembly at least partially disposed in the housing and coupled to the needle assembly. The needle assembly includes a needle or cannula and a sterile barrier disposed proximal to the needle or cannula in a first configuration where the sterile barrier is intact. The drive assembly includes a container that contains a medicament to be administered, a first plunger disposed in the container, and a drive mechanism that forces the first plunger to urge
(Continued)

the medicament through the container. Upon engaging the drive mechanism, the needle or cannula and the sterile barrier move relative to each other from the first configuration to a second configuration where the needle or cannula breaks the sterile barrier, thereby allowing the medicament to be administered via the needle or cannula.

5 Claims, 15 Drawing Sheets

(51) Int. Cl.
*A61M 5/315* (2006.01)
*A61M 5/32* (2006.01)
*A61M 5/34* (2006.01)

(56) References Cited

U.S. PATENT DOCUMENTS

| | | | | |
|---|---|---|---|---|
| 5,391,151 | A * | 2/1995 | Wilmot | A61M 5/2066 604/135 |
| 7,195,610 | B1 * | 3/2007 | Flachbart | A61M 25/10184 604/99.01 |
| 9,393,370 | B2 * | 7/2016 | Auld | A61F 9/0017 |
| 2007/0233019 | A1 * | 10/2007 | Forsell | A61M 5/14276 604/288.03 |
| 2009/0247940 | A1 | 10/2009 | Williamson et al. | |
| 2012/0010594 | A1 * | 1/2012 | Holt | A61M 5/14248 604/151 |
| 2015/0335817 | A1 | 11/2015 | Lambert | |
| 2016/0243309 | A1 * | 8/2016 | Cupicha | A61M 5/31511 |

FOREIGN PATENT DOCUMENTS

| | | | | |
|---|---|---|---|---|
| GB | 2456245 | A | 7/2009 | |
| WO | WO-9721457 | A1 * | 6/1997 | A61M 5/14248 |
| WO | WO-2004094823 | A2 | 11/2004 | |

OTHER PUBLICATIONS

International Search Report of International Patent Application PCT/US2018/045467, dated Feb. 26, 2019.

* cited by examiner

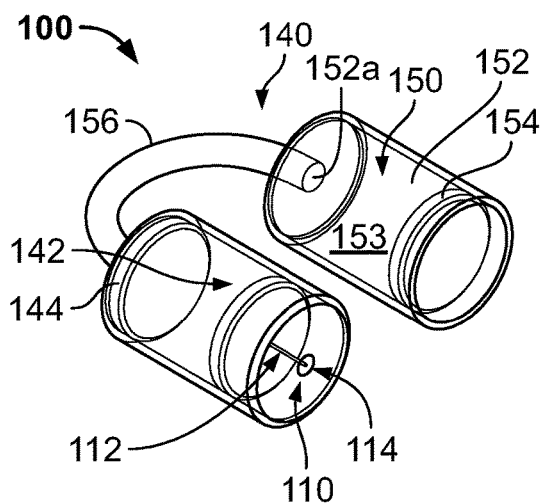
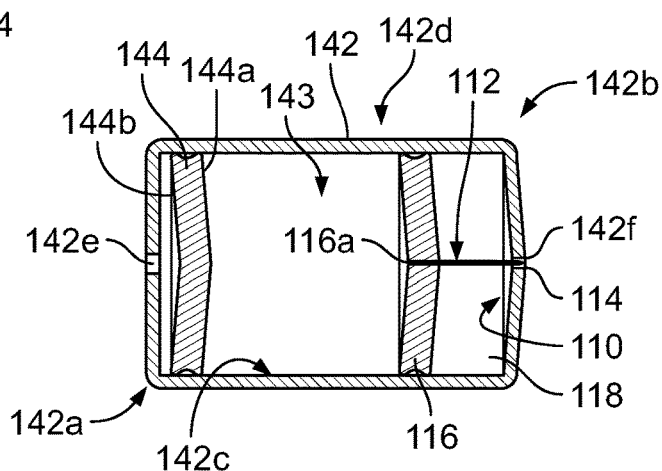
FIG. 2A
FIG. 2B
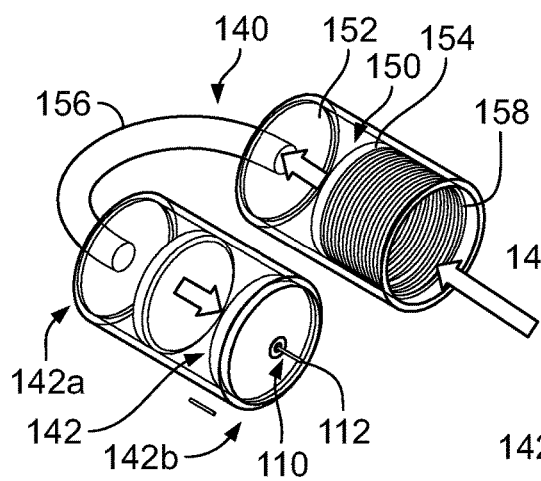
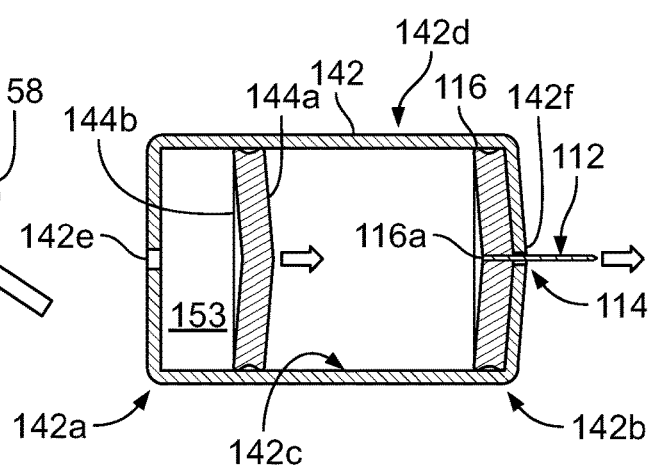
FIG. 3A
FIG. 3B
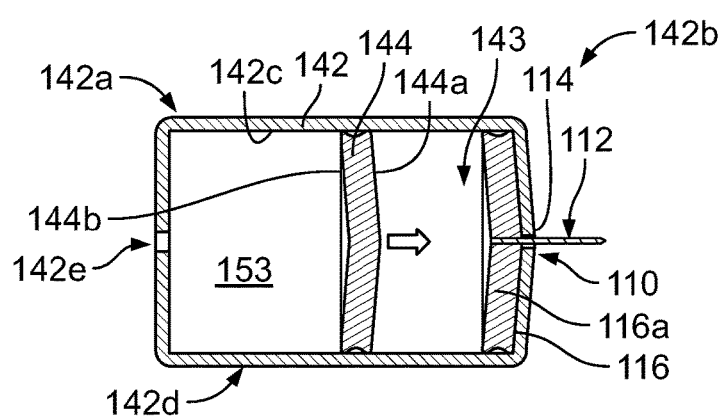
FIG. 3C

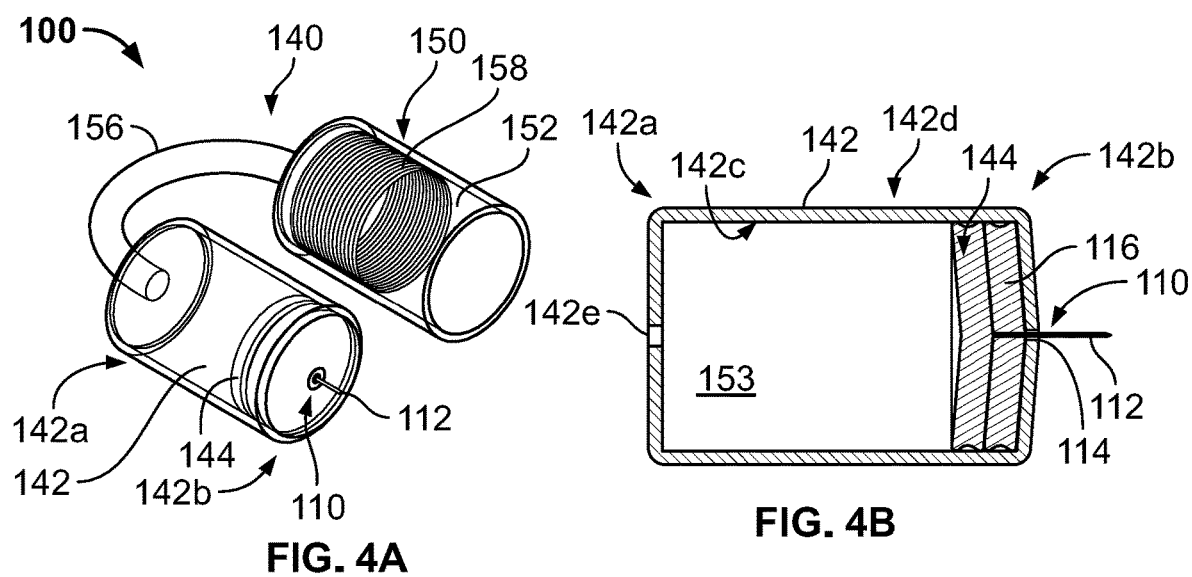
FIG. 4A
FIG. 4B
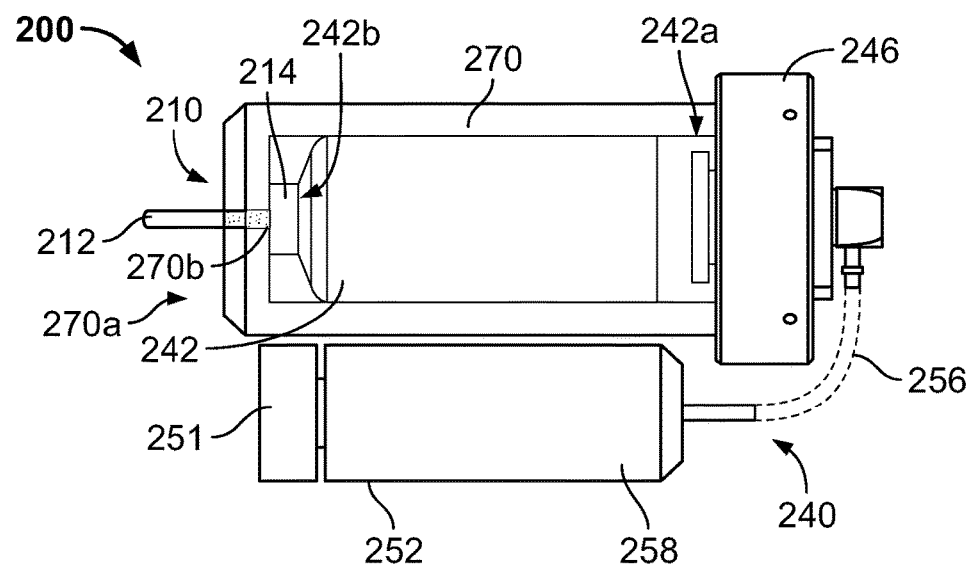
FIG. 5A

HYDRAULIC-PNEUMATIC PRESSURIZED CHAMBER DRUG DELIVERY SYSTEM

This is the United States national phase of International Patent Application No. PCT/US18/45467, filed Aug. 7, 2018, which claims priority to U.S. Provisional Patent Application No. 62/543,058, filed Aug. 9, 2017, the entire contents of each of which are incorporated herein by reference.

FIELD OF THE DISCLOSURE

The present disclosure generally relates to drug delivery devices and, more particularly, mechanisms and methods of delivery as well as inserting or deploying a needle and/or cannula of a drug delivery device.

BACKGROUND

Some drug delivery devices, such as on-body injectors, may be temporarily attached to a patient to deliver a drug via an injection needle or some other means over an extended period of time. The drug delivery device may be attached to the tissue of the patient's abdomen, thigh, arm, or some other portion of the patient's body.

In some cases, the drug delivery device may be worn by the patient for several minutes or hours while the drug is injected. For example, viscous drugs, including some biologics, can require substantial forces to expel the drug from the drug delivery device, and thus may have long injection times. Furthermore, some drug delivery devices are configured to be attached to the patient at a doctor's office, and then later deliver the drug to the patient when the patient returns to their home. For these reasons and others, a rigid injection member may be left inside the patient for a substantial amount of time, which can result in patient discomfort or unease.

In some examples, drug delivery devices include a first needle that penetrates the skin of the user, while another (or the same needle) overcomes a sterile barrier of the primary container that stores the medicament. The piercing of the sterile barrier may involve piercing a septum of a typical drug container. To simplify steps for the patient and to minimize user error, automated needle insertion and retraction is typically preferred. However, even when using automated systems, the injection process may involve multiple, potentially complex steps in order to properly administer the drug. As a result, insertion mechanisms have been disposed within drug delivery devices to accomplish insertion and/or retraction movements of the needle. Such an insertion mechanism, however, may increase the overall size, complexity, and/or cost of the drug delivery device.

Additionally, as higher viscosity drugs are delivered via drug delivery devices, requisite driving forces needed to dispense the drug will likely increase. These driving forces may place large amounts of stress on the primary container, and may break, crack, or otherwise damage the container during drug delivery.

SUMMARY

In accordance with a first aspect, a wearable drug delivery device includes a housing, a needle assembly at least partially disposed in the housing, and a drive assembly at least partially disposed in the housing and coupled to the needle assembly. The needle assembly includes a needle or cannula and a sterile barrier disposed proximal to the needle or cannula in a first configuration where the sterile barrier is intact. The drive assembly includes a container that contains a medicament to be administered, a first plunger disposed in the container, and a drive mechanism that forces the first plunger to urge the medicament through the container. Upon engaging the drive mechanism, the needle or cannula and the sterile barrier move relative to each other from the first configuration to a second configuration where the needle or cannula breaks the sterile barrier, thereby allowing the medicament to be administered via the needle or cannula.

In some examples, upon engaging the drive mechanism, the first plunger urges the medicament towards the second end of the container such that the medicament exerts a force that moves the needle or cannula and the sterile barrier relative to each other to the second configuration.

In these aspects, the container has a first end, a second end, an inner surface that defines an inner volume, and an outer surface. The first plunger and the inner surface of the container cooperate to encapsulate the medicament. The drive assembly may also include an outer shell that at least partially surrounds the container to define a pressure equalizing chamber therebetween. In these examples, the drive mechanism further exerts an equalizing pressure on the outer surface of the container that is approximately equal to the force exerted on the first plunger.

In some aspects, the drive mechanism may be a pneumatic and/or a hydraulic driving system. Specifically, the drive mechanism may be in the form of a pressurized gas chamber that, when engaged, releases a pressurized gas that exerts a force on the first plunger. In other examples, the drive mechanism may be in the form of a resilient member that urges a hydraulic fluid towards the first plunger.

In some forms, the sterile barrier may be disposed near the second end of the container. For example, the sterile barrier may be disposed on a second plunger positioned near the second end of the container. This second plunger may be urged by the medicament towards the second end of the container, thereby moving the needle or cannula and the sterile barrier to the second configuration to break the sterile barrier. In other examples, the device may further include a second plunger positioned near the second end of the container. In these examples, the needle or cannula is coupled to the second plunger, and the second plunger and the needle or cannula are adapted to move toward and puncture the sterile barrier upon being urged by the medicament towards the second end of the container.

In some aspects, the drive assembly further includes an urging component disposed at the first end of the container. The urging component urges the first plunger towards the second end of the container and causes the drive mechanism to exert the equalizing force on the outer surface of the container. The urging component may be in the form of an inflatable elastic member and/or an elastomeric pusher member. The elastomeric pusher member may include a sealing surface that restricts a driving fluid from contacting the medicament stored in the container.

In some examples, the device may further include a release mechanism operably coupled to the first plunger to at least partially relieve the first plunger from being urged towards the end of the container.

In accordance with a second aspect, a drive assembly for a wearable drug delivery device includes a container having a first end, a second end, an inner surface, and an outer surface, a first plunger being disposed in the first end of the container, a pressure chamber at least partially surrounding the container to define a pressure equalizing chamber therebetween, and a drive mechanism. An inner volume of the container is adapted to contain a medicament to be administered to a user. The first plunger has a first surface and a second surface. The first surface of the first plunger and the inner surface of the container cooperate to form a fluid tight seal that encapsulates the medicament within the container. The pressure chamber is sealed and in fluid communication with the second surface of the first plunger such that the pressure chamber is subject to equal pressure as an inner volume of the container.

The drive mechanism includes a drive container that contains a drive fluid and a drive connection that fluidly connects the drive container and the container. Upon actuating the drive mechanism, the drive fluid exerts on the second surface of the first plunger to urge the medicament through the container and exerts an equalizing pressure on the outer surface of the container that is approximately equal to the force exerted on the first plunger.

In some examples, the fluid activation mechanism consists of a torsional spring that drives a pressurized gas capsule towards a fixed spike to provide the driving force for the medicament dispensing. Upon activating the trigger button, the torsional spring drives the capsule axially forward toward a fixed spike where a thin metal film sealing the capsule is punctured to release the gas from the capsule. The released gas is routed to the back of the plunger in the primary container to initiate drug dispensing. At the same time, the released gas envelops the primary container through a secondary enclosure to equalize the inner and outer pressure of the primary container. This will prevent potential failure of the primary container regardless of materials makeup in the case of over pressurization or in situations requiring large pressures to expel high viscosity medicament through narrow gauge needles.

In accordance with a third aspect, a pressure drive system for a wearable drug delivery device includes a primary container for storing a medicament to be administered to a user, a sealed pressure chamber at least partially surrounding the primary container, a cannula insertion mechanism in fluid connection with the primary container, and an activation mechanism in fluid connection with the cannula insertion mechanism and the primary container. The cannula insertion mechanism is adapted to insert a cannula into the user to inject the medicament. The activation mechanism is adapted to cause the cannula insertion mechanism to insert the cannula into the user, and is further adapted to cause the medicament to be dispensed. Upon activating the activation mechanism, a pressure is delivered to the cannula insertion mechanism to displace the cannula. The pressure is further delivered to 1) the primary container to urge the medicament to the cannula insertion mechanism; and 2) the pressure chamber to exert an opposing pressure on an outer sidewall of the primary container.

BRIEF DESCRIPTION OF THE DRAWINGS

The above needs are at least partially met through provision of the hydraulic-pneumatic pressurized chamber drug delivery system described in the following detailed description, particularly when studied in conjunction with the drawings, wherein:

FIGS. 2a and 2b illustrate an example pneumatically driven drive assembly for a wearable drug delivery device in a first, starting position in accordance with various embodiments;

FIGS. 3a-3c illustrate the example drive assembly of FIGS. 2a and 2b during the drug administration process in accordance with various embodiments;

FIGS. 4a and 4b illustrate the example drive assembly of FIGS. 2a-3c upon completion of the drug being administered in accordance with various embodiments;

FIGS. 5a and 5b illustrate an example pressure driven drive assembly for a wearable drug delivery device in a first, starting position in accordance with various embodiments;

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. It will further be appreciated that certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Figure 1:
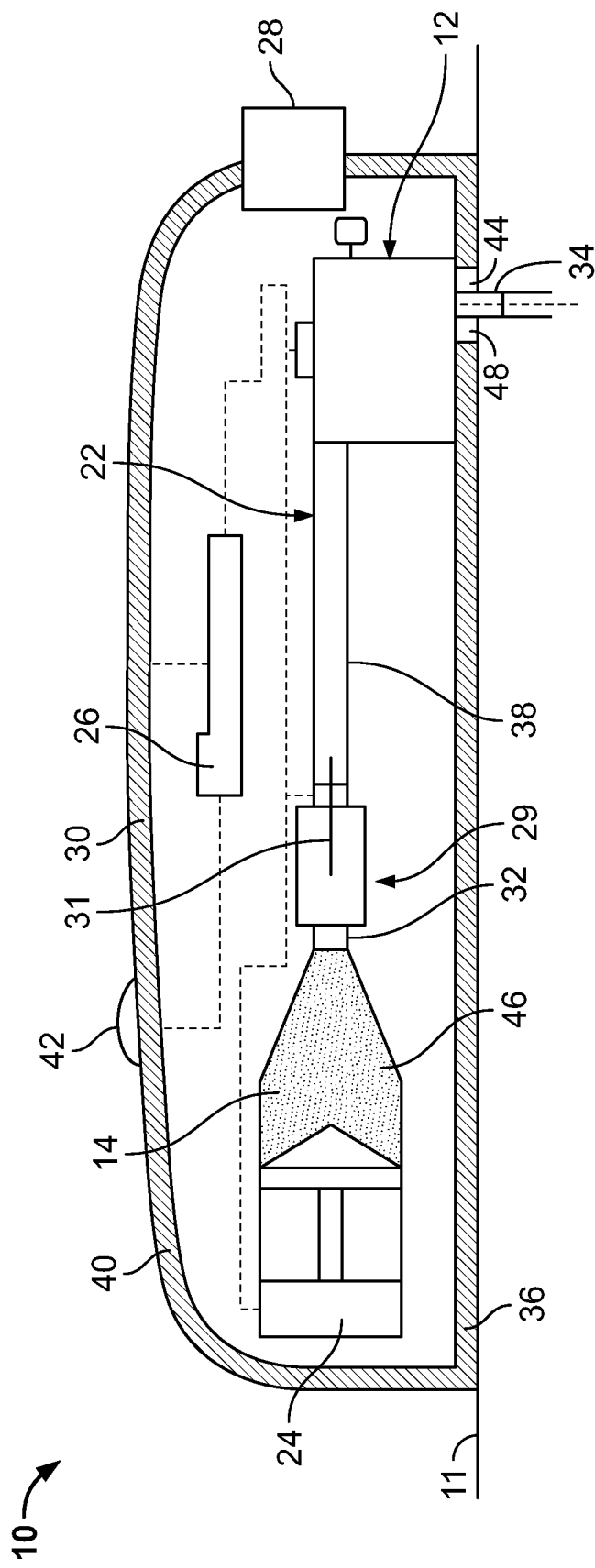
FIG. 1 illustrates a schematic representation of an example arrangement of a drug delivery device having a hydraulic-pneumatic pressurized chamber drug delivery system in accordance with various embodiments.

Referring to FIG. 1, a general wearable drug delivery device 10 is provided that may include any number of aspects of the hydraulic-pneumatic pressurized chamber drug delivery system herein described. In at least one example, the drug delivery device 10 may be configured as a wearable drug delivery device, such as an on-body injector, that may be attached to a patient's tissue 11 (e.g., the patient's skin) to administer delivery of a drug treatment. The drug delivery device 10 may automatically deliver a subcutaneous injection of a fixed or a patient/operator-settable dose of a drug over a controlled or selected period of time. The drug delivery device 10 may be intended for self-administration by the patient, but may also be used by a caregiver or a formally trained healthcare provider to administer an injection.

The drug delivery device 10 has a needle insertion assembly 12, a container 14 coupled to the needle insertion assembly 12 by a fluid pathway connector 22, a drive assembly 24, and a controller 26, each of which may be disposed in a main housing 30 defining a shell of the drug delivery device 10. An actuator 28 (e.g., a depressible button) may be arranged on an exterior of the main housing 30 and configured to initiate operation of the drug delivery device 10 by activating the drive assembly 24, the needle insertion assembly 12, and/or the controller 26 via mechanical and/or electrical means (shown in dotted lines in FIG. 1). The fluid pathway connector 22 defines a sterile fluid flow path 38 between the container 14 and the needle insertion assembly 12. The fluid pathway connector 22 may include a container access mechanism 29 configured to insert a container needle 31 through a septum 32 associated with and covering the container 14 to establish fluid communication between the container 14 and the sterile fluid flow path 38 in response to activation of the drug delivery device 10, for example, via the actuator 28. In some examples, and as will be discussed, the needle insertion assembly 12 and the container 14 may be integrated into a single unit, and thus the fluid pathway connector 22 may not be incorporated into the drug delivery device 10.

The main housing 30 may include a bottom wall 36 to be releasably attached (e.g., adhered with an adhesive) to the patient's skin 11, and a top wall 40 including one or more indicator lights 42 and/or a window (not illustrated) for viewing the container 14. An opening 44 may be formed in the bottom wall 36, and optionally a septum 48 may extend across the opening 44 to seal the interior of the main housing 30 prior to use. The exterior of the needle insertion assembly 12 may be defined by an insertion/retraction mechanism housing separate from the main housing 30, as explained more below relative to each example needle insertion assembly 12.

Generally, upon activation of the drug delivery device 10, the drug delivery device 10 may enable, connect, or open necessary connections to establish fluid communication between the container 14 and the fluid pathway connector 22. Simultaneously or subsequently, the needle insertion assembly 12 may insert a needle 34 into the patient 11, which may be a rigid or a flexible needle. In examples using a flexible needle, the flexible needle may be made of a super-elastic material such as nitinol, a polymer, or another material that allows the needle to follow a curved path without sustaining damage. Next, the drive mechanism 24 may force a drug 46 stored in the container 14 through the sterile fluid flow path 38 of the fluid pathway connector 22 and into the needle insertion assembly 12 for subcutaneous delivery to the patient.

Turning to FIGS. 2a-2c, a hydraulic and/or pneumatic drive force is used to achieve needle piercing of the primary container septum as well as penetration into the skin to establish a complete fluidic path for drug delivery. The illustrated device 100 can include the housing 30 of FIG. 1 defining a shell, a needle assembly 110 at least partially disposed within the housing, and a drive assembly 140 that includes a drive mechanism 150 (i.e., a spring driven driving mechanism) also at least partially disposed within the housing that is operably coupled to the needle assembly 110. Although configured for use with the drug delivery device 10 depicted in FIG. 1, needle and drive assemblies 110, 140 are separate components that are compatible with a variety of drug delivery devices not herein described. The needle assembly 110 includes a needle or cannula 112 and a sterile barrier 114 disposed proximal or near the needle or cannula 112. In the illustrated examples of FIGS. 2a-4b, the device uses direct pressure to pressurize the chamber.

The drive assembly 140 includes a container 142 having a first end 142a, a second end 142b, an inner surface 142c, and an outer surface 142d. The container 142 defines an inner volume to contain a medicament 143 to be delivered to a user. The drive assembly 140 further includes a first plunger 144 which is disposed within the container 142 at the first end 142a thereof. The first plunger 144 has a first surface 144a and a second surface 144b. The first surface 144a of the first plunger 144 and the inner surface 142c of the container 142 cooperate to encapsulate the medicament 143 within the container 142. In other words, the first plunger 144 acts as a seal that restricts the medicament 143 from exiting the first end 142a of the container 142.

The drive assembly 140 includes a drive mechanism 150 that exerts an urging force on the first plunger 144. The drive mechanism 150 includes a drive container 152 containing a hydraulic fluid 153, a drive plunger 154, and a drive connection 156. The drive connection 156 provides a fluid flow path between the container 142 and the drive container 152. In the illustrated example, the drive connection 156 is a hose or tube that couples to the container 142 and the drive container 152 via respective openings 142e, 152a. Other examples of suitable connectors and respective connections are possible In the illustrated example of FIGS. 2a and 2b, the needle assembly 110 is at least partially disposed within the container 142. Specifically, the needle or cannula 112 is coupled to a second plunger 116 at or near the second end 142b of the container 140. The needle or cannula 112 is in fluid communication with the medicament 143 via an opening 116a on the second plunger 116. The first plunger 144 and the second plunger 116 both act as seals to restrict movement of the medicament 143 inside the container 142. Further, in a first configuration, the needle or cannula 112 is disposed near the sterile barrier 114, thus the medicament 143 is restricted from entering the void 118 between the second plunger 116 and the first end 142b of the container. The needle or cannula 112 and the sterile barrier 144 are movable relative to each other.

The sterile barrier 114 is disposed at a second opening 142f of the container 142. In some examples, the sterile barrier 114 is disposed on the outer surface 142d of the container 142, and in other examples, the sterile barrier 114 is disposed on the inner surface 142c of the container 142. Other examples of suitable locations and/or configurations of the sterile barrier 114 are possible, and will be discussed with relation to various embodiments below.

In FIGS. 2a and 2b, the hydraulic fluid 153 has no external forces acting on it, thus the drive assembly 140 is in a starting state where the needle or cannula 112 is fully retracted. In FIGS. 3a and 3b, the drive mechanism 150 has been actuated via any number of suitable approaches. As such, the first plunger 144 urges the medicament 143 towards the second end 142b of the container 142. Specifically, as illustrated in FIG. 3a, an external drive mechanism such as a resilient member or spring 158 exerts a force on the drive plunger 154 that pressurizes the hydraulic fluid 153. This pressure is transmitted via the drive connection 156 to the first plunger 144, which then exerts a force on the medicament 143. Accordingly, the medicament 143 is urged towards the second plunger 116.

As illustrated in FIG. 3b, the hydraulic fluid 153 is continually urged towards and against the first plunger 144, and thereby enters an area between the first plunger 144 and the first end 142a of the container 142. Further, the continued urging by the first plunger 144 causes the medicament 143 to exert a force on the second plunger 116, to which the needle or cannula 112 is coupled. When a substantial force is exerted on the second plunger 116, the second plunger 116 (and the needle or cannula 112) will advance towards the second end 142b of the container 142. Accordingly, the needle or cannula 112 and the sterile barrier 114 move relative to each other to a second configuration where the needle or cannula 112 punctures or breaks the sterile barrier 114, thereby allowing the needle or cannula 112 to be injected into a user and the medicament 143 to be administered via the needle or cannula 112.

As illustrated in FIG. 3c, the first plunger 144 continues to advance towards the second end 142b of the container 142, thus continues to the medicament 143 through the needle or cannula 112 to be delivered. As illustrated in FIGS. 4a and 4b, the first plunger 144 reaches the end of its stroke (and is in contact with the second plunger 116, thus the full volume of the medicament 143 is delivered. In some examples (not shown), the drive assembly 140 may further include a release mechanism that exerts an opposing force on the first plunger 144 that causes the first plunger 144 and the second plunger 116 to move towards the first end 142a of the container 142. Accordingly, the needle or cannula 112 will be retracted and removed from the user.

As illustrated in FIGS. 5a-10, an alternate drug delivery device 200 is provided. The drug delivery device 200 includes similar features and elements as the drug delivery device 100, and thus has reference numerals with identical two-digit suffixes as those in the drug delivery device 100 of FIGS. 2-4b. As such, for the sake of brevity, similar components will not be described in detail. The drug delivery device 200 may include additional components not illustrated in the Figures. In the illustrated examples of FIGS. 5a-11 (and 14-15b), the device uses indirect pressure to pressurize the chamber.

The drug delivery device 200 includes the pressure chamber 270, and a drive assembly 240 that includes a drive mechanism 250 (e.g., a pneumatic, hydraulic, and/or spring driven driving mechanism). The pressure chamber 270 includes a needle assembly 210, which includes a needle or cannula 212 and a sterile barrier 214. Inside the pressure chamber 270 is a container 242 having a first end 242a, a second end 242b, an inner surface 242c, and an outer surface 242d and is adapted to store a medicament 243 in an inner volume thereof. The medicament container 242 further includes a first plunger or stopper 244 having a first surface 244a and a second surface 244b and an insert 246. The plunger 244 is at least partially disposed in the container 242. In the illustrated example, the pressure chamber 270 is in the form of an outer shell that at least partially surrounds the container 242 to define a pressure equalizing chamber therebetween, and allows lateral movement of the container 242 within a volume or gap 272 of the pressure chamber 270. In other words, the pressure chamber 270 is dimensioned to create a gap between the outer surface 242d of the container 242 and the pressure chamber 270. In some examples, the gap 272 may be filled with water or a different fluid to allow pressure to be applied to the liquid, thereby forcing the plunger to dispense them medicament and resulting in a combination pneumatic-hydraulic application. The pressure chamber 270 is sealed and in fluid communication with the second surface 244b of the first plunger 244 such that the pressure chamber 270 is subject to equal pressure as an inner volume of the container 242.

The insert 246 is disposed at the first end 242a of the container 242 and includes an opening or channel 246a disposed through the insert 246, a sealing member 246b (e.g., an O-ring), and a gas inlet or passageway 246c. The insert 246 is inserted in a first end 270a of the pressure chamber 270 such that the insert seal 246b contacts an inner surface of the pressure chamber 270 to create a seal.

The drive assembly 240 includes a pneumatic drive mechanism 250 in the form of a gas source that creates an urging force, and includes an actuator button or screw 251, a drive container 252 coupled to the actuator screw 251 that contains a gas cartridge 253 that stores a drive fluid such as compressed gas 253a, a gas cartridge spike portion 254, and a drive connection 256 (e.g., a gas outlet) formed between the drive mechanism 250 and the container 240 and includes a compressed gas spike 256a. In some examples, the gas can be a compressed gas, such as nitrogen or argon, or a liquefied gas, such as $CO_2$ or $SF_6$. In other examples, the gas can also be a liquefied propellant, such as HFC-134a (hydrofluorocarbon).

In the illustrated example, the needle or cannula 212 is fixedly disposed through an opening 270b on a first end 270a of the pressure chamber 270. Briefly summarizing operation of the drug delivery device 200, upon actuating the drive mechanism 250, the drive fluid 253a exerts a force on the second surface 244b of the first plunger 244 to urge the medicament 243 through the container 242, and exerts an equalizing pressure on the outer surface 242d of the container 242 that is approximately equal to the force exerted on the first plunger 244. Further, the drive fluid 253a causes the container 242 to advance towards the first end 270a of the pressure chamber 270, where the needle or cannula 212 punctures the sterile barrier 214. The first plunger 244 then urges the medicament 243 through the needle or cannula 212 to be administered to the user.

Figure 5B:
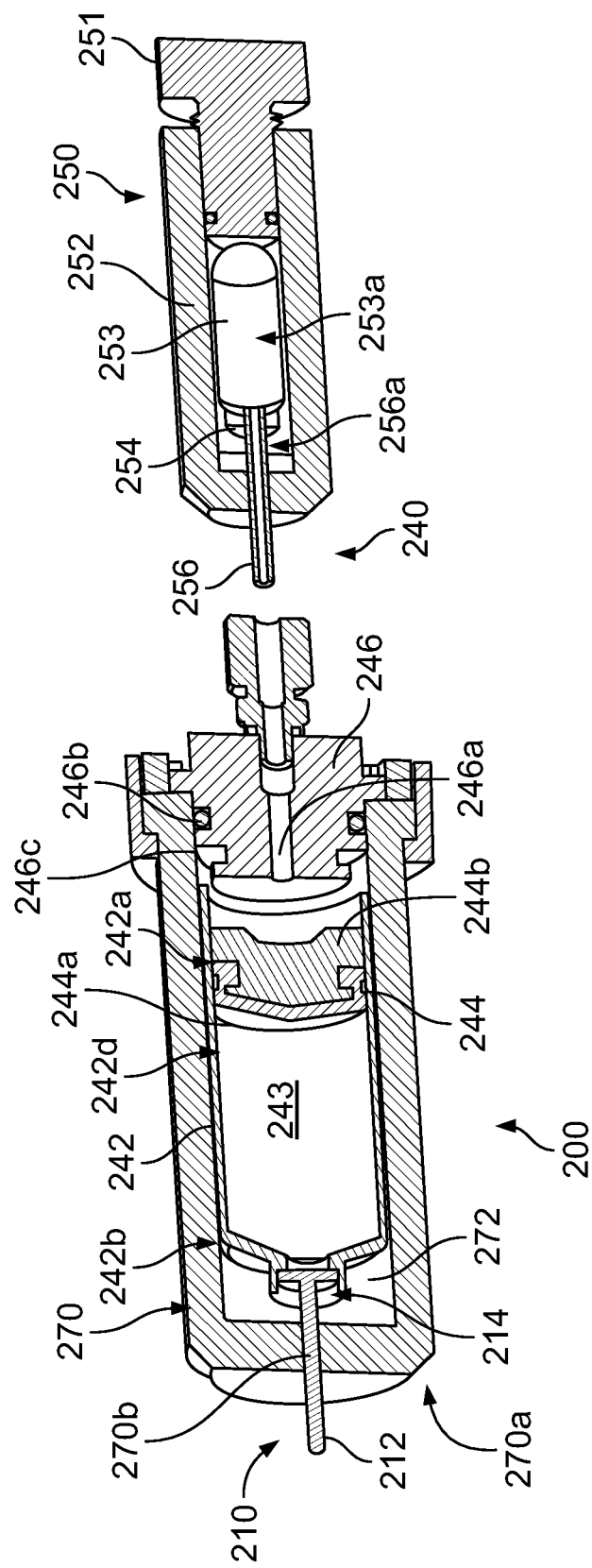

More specifically, with reference to FIG. 5b, the actuator screw 251 is first turned. In some examples, turning of the actuator screw 251 occurs by pressing or depressing the actuator screw 251 in a direction towards the gas cartridge 253. This movement in turn causes the gas cartridge 253 to be urged towards the compressed gas spike 256a, which will pierce the gas cartridge spike portion 254, thereby causing the compressed gas 253a to flow through the drive connection 256 towards the pressure chamber 270.

Figure 6:
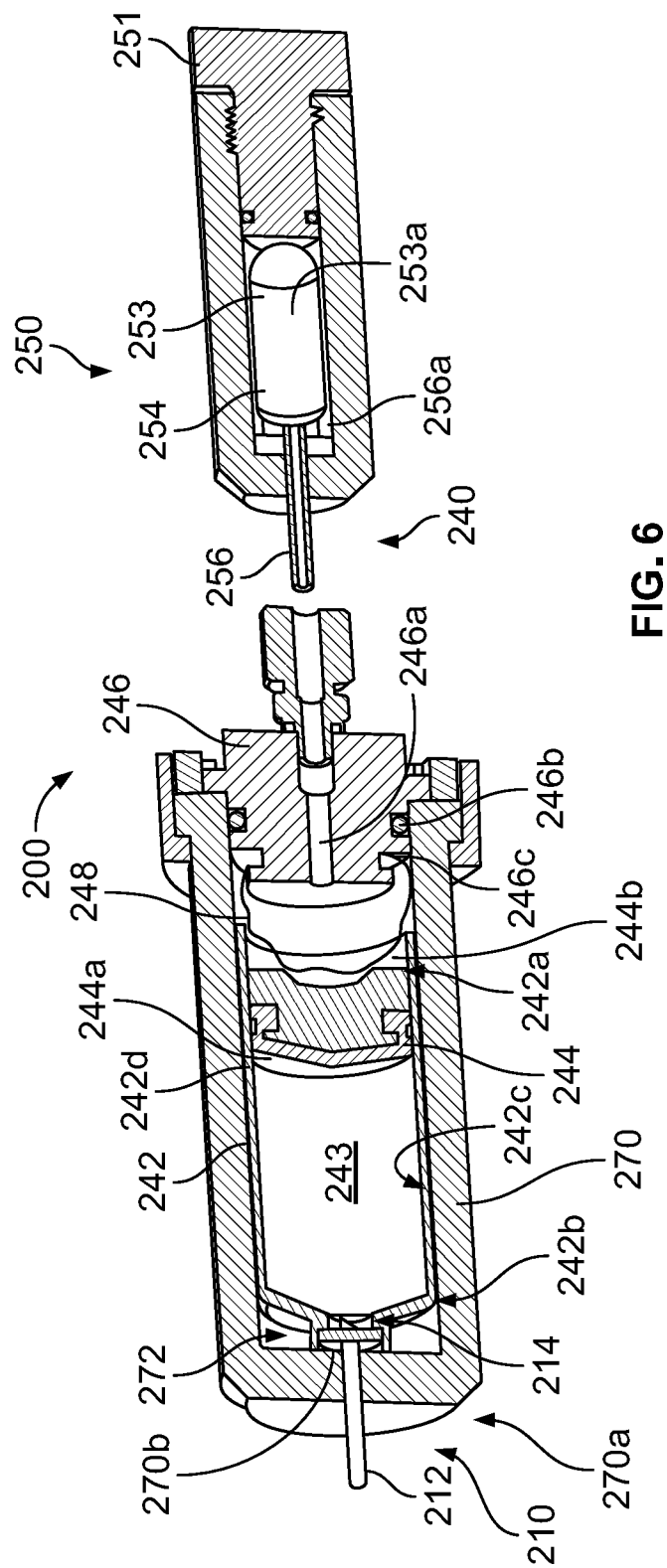
FIG. 6 illustrates the example pressure driven drive assembly of FIGS. 5a and 5b having an inflatable urging component in accordance with various embodiments.

As illustrated in FIG. 6, the pressurized gas 253a then flows through the insert 246 and contacts an urging component 248. In the illustrated embodiment, the urging component 248 is an inflatable balloon. In this example, the urging component 248 inflates and exerts a force on the first plunger 244 that causes the container 242 to advance towards the first end 270a of the pressure chamber (and thus advance toward the needle or cannula 212). The first plunger 244 then pushes the container 242 onto the needle or cannula 212 to break the sterile barrier 214. The compressed gas 253a continues to urge the first plunger 244 towards the second end 242b of the container 242, thereby continuing delivery of the medicament 243. Accordingly, the medicament 243 may flow through the needle or cannula 212 to be administered to a user. In some examples, the urging component 248 may not be used, and the pressurized gas 253a may directly contact the first plunger 244.

When the container 242 advances toward the first end 270a of the pressure chamber 270, a flow path is created that allows the compressed gas 253a to flow through the insert passageway 246c and into the area surrounding the outer surface 242d of the container 242 and into the pressure chamber volume 272. So configured, the compressed gas 253a exerts an equalizing pressure on the outer surface 242d of the container 242. This equalizing force is approximately equal to the force exerted on the first plunger 244 and limits the effect of the pressure generated inside of the container 242, thereby reducing and/or eliminating the likelihood of the container becoming over pressurized. Accordingly, large pressures can be applied without causing failure of the primary container to dispense high viscosity medicament 243 using a small needle or cannula 212 in a short time span on par with typical autoinjectors. Further, the equalizing pressure allows for large volume delivery of medicament 243 since it allows for high pressure gases to be used to deliver the volume of the medicament 243. Compressed gas 253a also can allow for slower delivery rate of the medicament 243 if desired. Additionally, the delivery state of the pressure chamber 253 upon delivery of the medicament 243 can be determined using the distinct pressure profile during various stages of delivery (e.g., during septum penetration, needle insertion into the skin, delivery initiation, sustenance, and delivery completion). These distinct pressure profiles can be readily detected by a pressure transducer disposed along gas channels and/or hydraulic-pneumatic chambers and fluidic channels.

Figure 7:
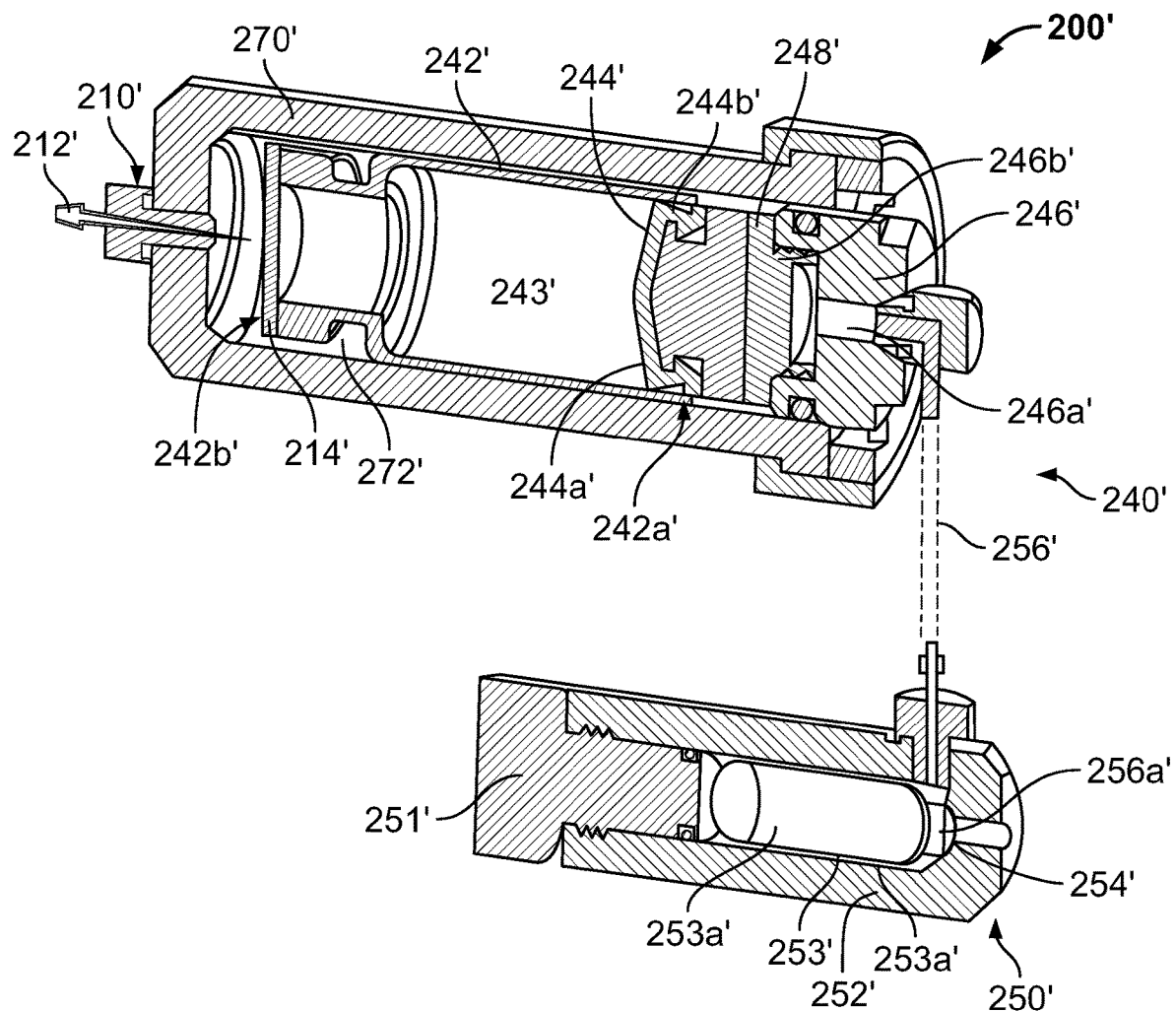
FIG. 7 illustrates the example pressure driven drive assembly of FIGS. 5a and 5b having an elastomeric pusher member in accordance with various embodiments.
Figure 8:
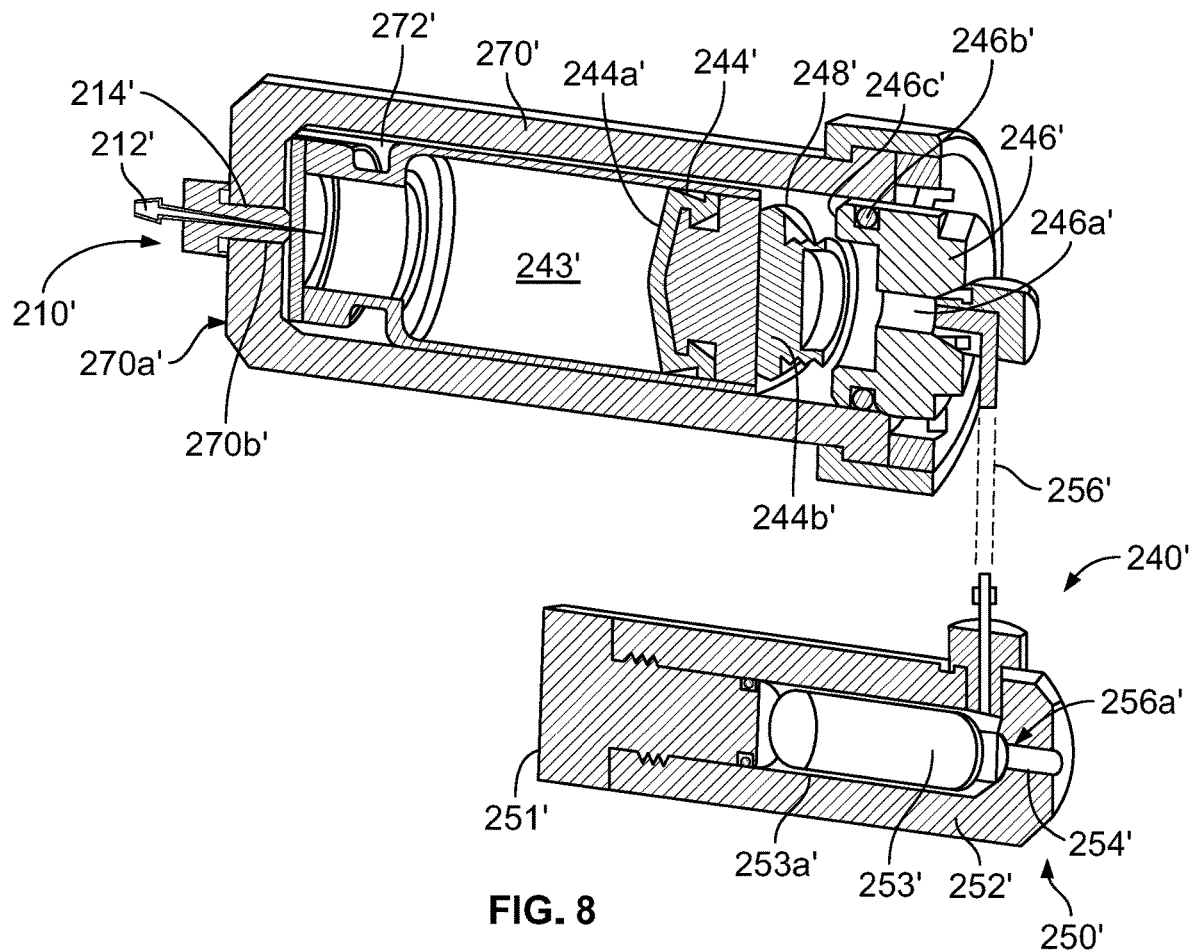
FIG. 8 illustrates the example pressure driven drive assembly of FIG. 7 upon being actuated in accordance with various embodiments.
Figure 9:
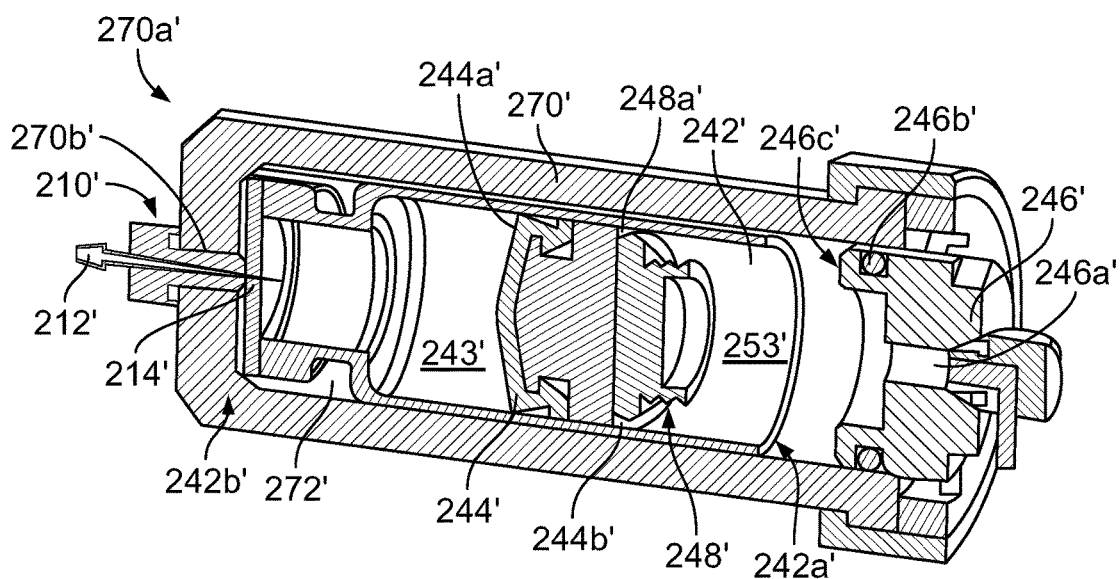
FIG. 9 illustrates the example pressure driven drive assembly of FIGS. 7 and 8 during delivery of the drug in accordance with various embodiments.

Turning to FIGS. 7-9, a drug delivery device 200' is provided that includes similar features as the drug delivery device 200 of FIGS. 5a-6. These features are depicted with identical reference characters as those provided with regards to FIGS. 5a-6 and have a prime symbol (') appended thereto. The drug delivery device 200' may include additional components not illustrated in the Figures. However, in this example, the urging component 248' is in the form of an elastomeric pusher member. As with the drug delivery device 200 of FIGS. 5a-6 and as illustrated in FIG. 8, upon actuating the actuator button 251', the gas cartridge 253a' advances towards the compressed gas spike 256a' which spikes the gas cartridge spike portion 254' to allow the gas cartridge 253' to advance through the drive connection 256'. The urging component 248' (shown before use in FIG. 7) forces the container 242' onto the needle or cannula 212' (as illustrated in FIG. 8), thereby breaking the sterile barrier 214', and subsequently or simultaneously allows the pressurized gas 253a' to flow into the pressure chamber volume 272'. As illustrated in FIG. 9, the urging component 248' follows the first plunger 244' and provides an additional gas seal via an outer sealing surface 248a' to ensure the compressed gas 253a' does not come into contact with the medicament 243'

Figure 10:
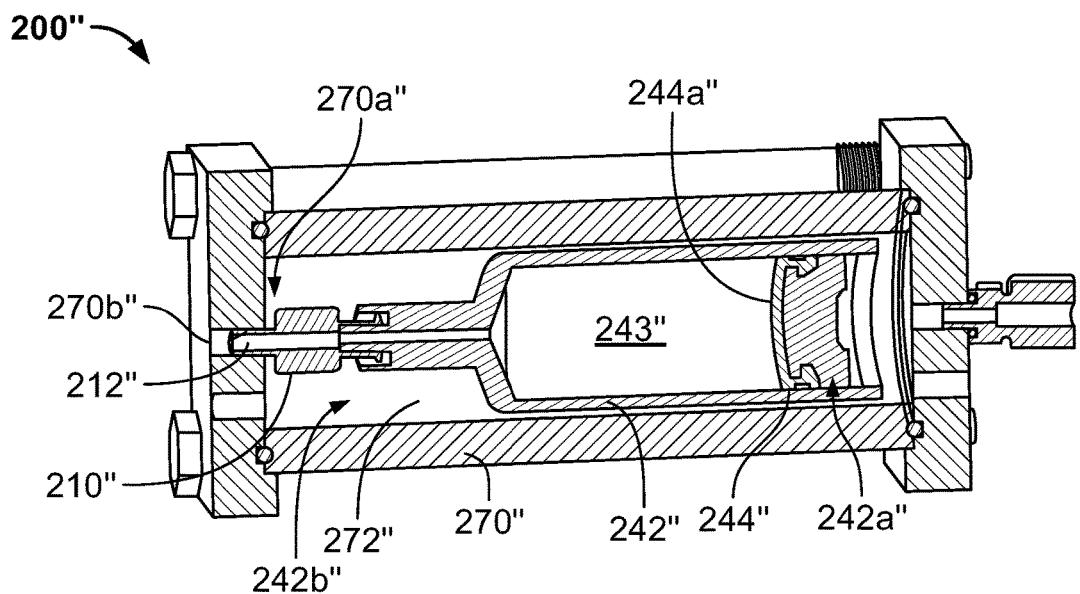
FIG. 10 illustrates an example pressure driven drive assembly that uses a glass syringe in accordance with various embodiments.
Figure 11:
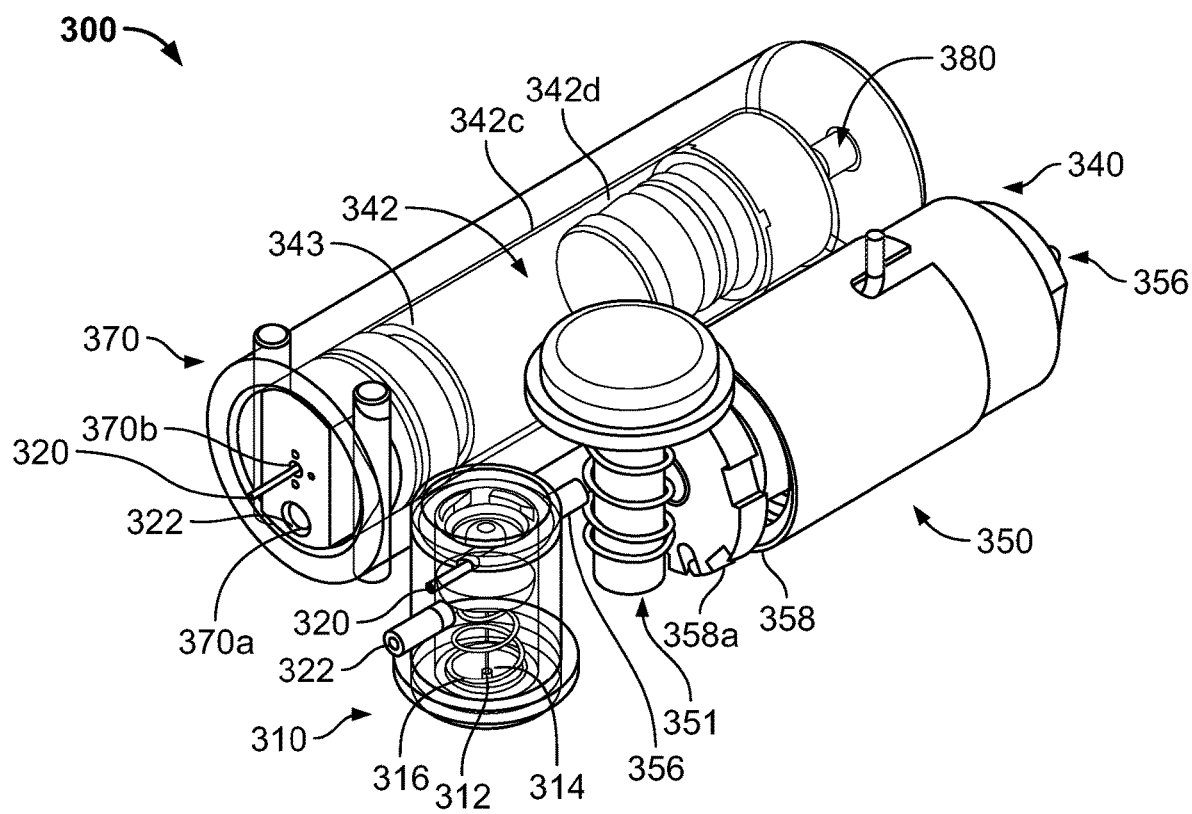
FIG. 11 illustrates an example pressure drive system for a wearable drug delivery device in accordance with various embodiments.

Turning to FIG. 10, an alternate drug delivery device 200" is provided that includes similar features as the drug delivery device 200. The drug delivery device 200" may include additional components not illustrated in the Figures. However, in this example, the container 242" is in the form of a conventional glass syringe which may be readily available. Accordingly, FIG. 10 illustrates how the alternate drug delivery device 200" may be incorporated into a number of available devices and designs.

As illustrated in FIGS. 11-16, an alternate pressure drive system for a wearable drug delivery device 300 is provided. The system 300 includes similar features and elements as the drug delivery devices 100, 200, 200', and 200", and thus have reference numerals with identical two-digit suffixes as those in the drug delivery devices of FIGS. 2-10. As such, for the sake of brevity, similar components will not be described in detail. The system 300 may include additional components not illustrated in the Figures.

The system 300 includes a primary container 342 for storing a medicament 343 to be administered by a user, a sealed pressure chamber 370 at least partially surrounding the primary container 342, a cannula insertion mechanism 310 in fluid connection with the primary container 342, and an activation mechanism 340 in fluid connection with the cannula insertion mechanism 310 and the primary container 342.

Figure 12A:
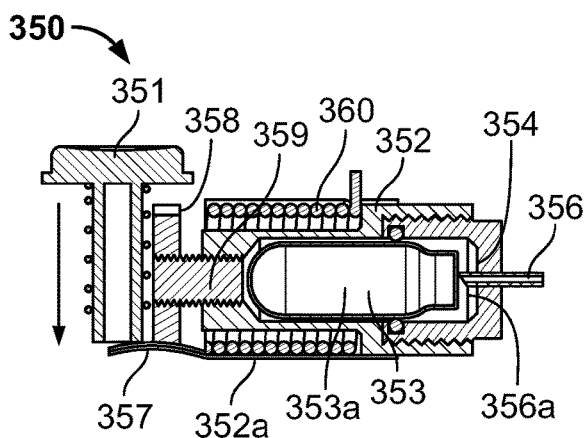
FIGS. 12a-12c illustrate an example actuation process of the pressure drive system of FIG. 11 in accordance with various embodiments.
Figure 12B:
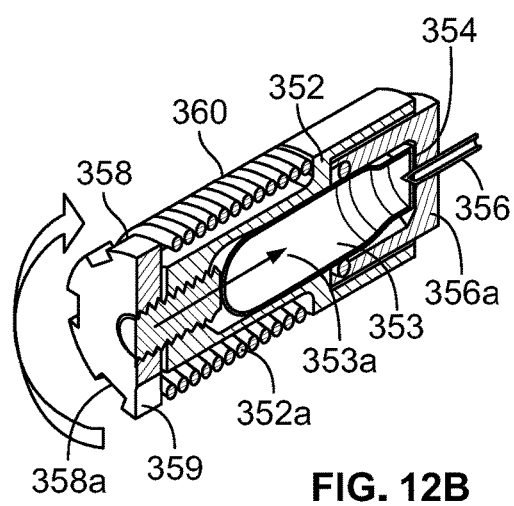
Figure 12C:
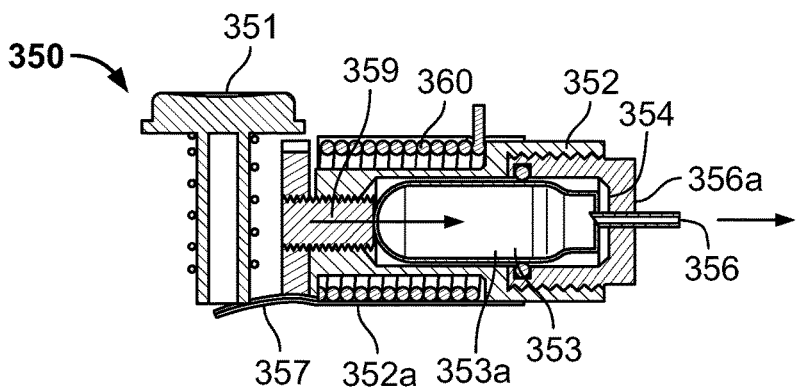

The activation mechanism 350 is adapted to cause the cannula insertion mechanism 310 to insert the needle or cannula 312 into the user and to cause the medicament 343 to be dispersed. As illustrated in FIGS. 12a-12c, the activation mechanism 350 includes an actuator button 351, a drive container 352 having a threaded portion 352a, a gas cartridge 353 disposed within the drive container 352 that stores a compressed gas 353a, a gas cartridge spike portion 354, and a first connection 356 having a cartridge spike 356a. The activation mechanism 350 further includes a locking tab 357, a gear 358 having a number of catches 358a, a threaded drive screw 359 coupled to the gear 358, and a pretensioned spring 360 also operably coupled to the gear 358. Generally, the spring 360, the gear 358, and the threaded drive screw 359 cooperate to that advance the gas cartridge 353 towards the cartridge spike 356a. The activation mechanism 350 can include any number of additional features to assist in actuating the system 300.

In operation, in a resting configuration, the spring 360 maintains a wound, loaded, or pretensioned state when the locking tab 357 engages one of the catches. This configuration prevents the threaded drive screw 359 from advancing into the drive container 352 until activation. Upon depressing the actuator button 351, the actuator button 351 urges the locking tab 357 downwards and away from one of the catches 358a. The locking tab 357 then releases from the catch 358a, thereby allowing the spring 360 to unwind. As the spring 360 unwinds, the gear 358 and the threaded drive screw 359 rotate relative to the threaded portion 352a of the drive container 352. This rotation causes the threaded drive screw 359 to advance into the drive container 352 to urge the gas cartridge 353 towards the cartridge spike 356a. The cartridge spike 356a will eventually puncture the gas cartridge spike portion 354, and thus, pressure from the compressed gas is delivered to the cannula insertion mechanism 310 via the first connection 356.

Figure 13A:
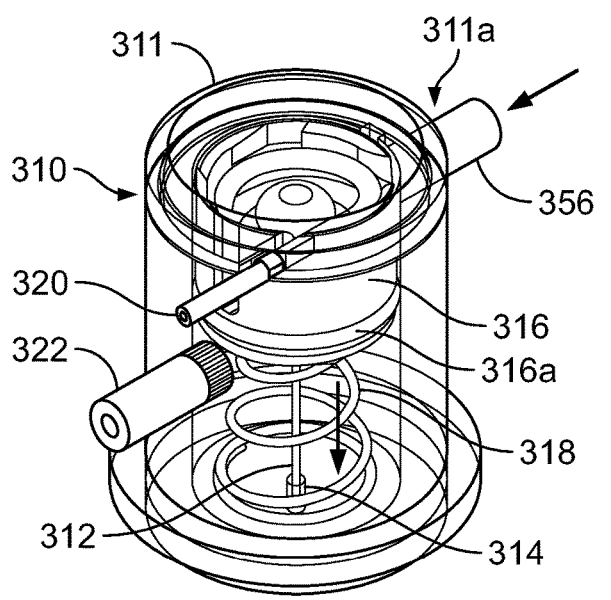
FIGS. 13a and 13b illustrate an example cannula insertion process of the pressure drive system of FIGS. 11-12c in accordance with various embodiments.
Figure 13B:
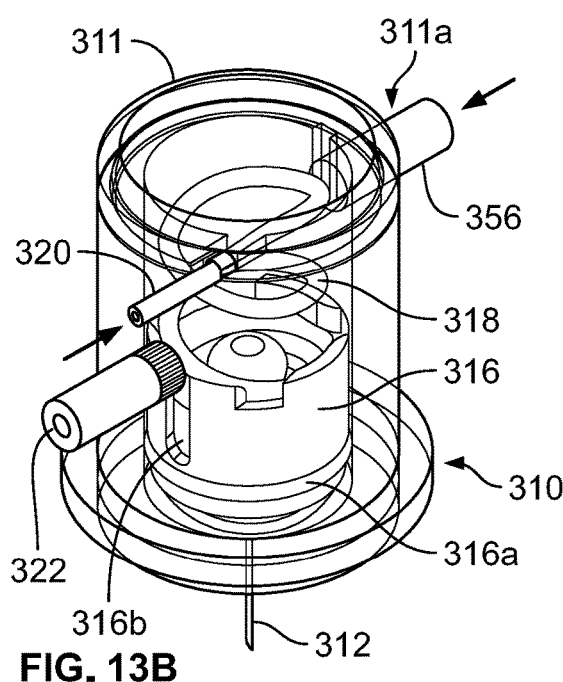

As illustrated in FIGS. 13a and 13b, the cannula insertion mechanism 310 is adapted to insert a needle or cannula 312 into the user to inject the medicament 343. The cannula insertion mechanism 310 includes a housing 311 defining a shell that includes an opening 311a to receive the first connection 356, a sliding plunger assembly 316 to which the cannula or needle 312 is attached, and a resilient member 318 that urges the sliding plunger assembly 316 in a first, non-inserted position. The sliding plunger assembly 316 includes a sealing surface 316a that seals the housing 311. The cannula insertion mechanism 310 further includes a second connection 320 that allows the medicament 343 to flow from the container 342 to the needle or cannula 312 and a third connection 322 to allow the compressed gas 353a to flow from the cannula insertion mechanism 310 to the pressure chamber 370.

In operation, and with reference to FIG. 13a, as the compressed gas 353a flows into the opening 311a, the sliding plunger assembly 316 overcomes a resistive force from the resilient member 318 and is urged downwards to eventually puncture the sterile barrier 314. This pressure is maintained by the compressed gas 353a, thus the sliding plunger assembly 316 remains in a second position where the needle or cannula 312 is inserted into a user.

As illustrated in FIG. 13b, as the sliding plunger assembly 316 advances downward, the sealing surface 316a becomes positioned below an opening corresponding to the third connection 322. In the illustrated example, the sliding plunger assembly 316 further includes a cutout or channel 316b to accommodate the third connection 322. Once the sealing surface 316a of the sliding plunger assembly 316 is positioned below the third connection 322, the compressed gas 353a may then pass through the third connection 322 and advance to the pressure chamber 370 and container 342.

Figure 14:
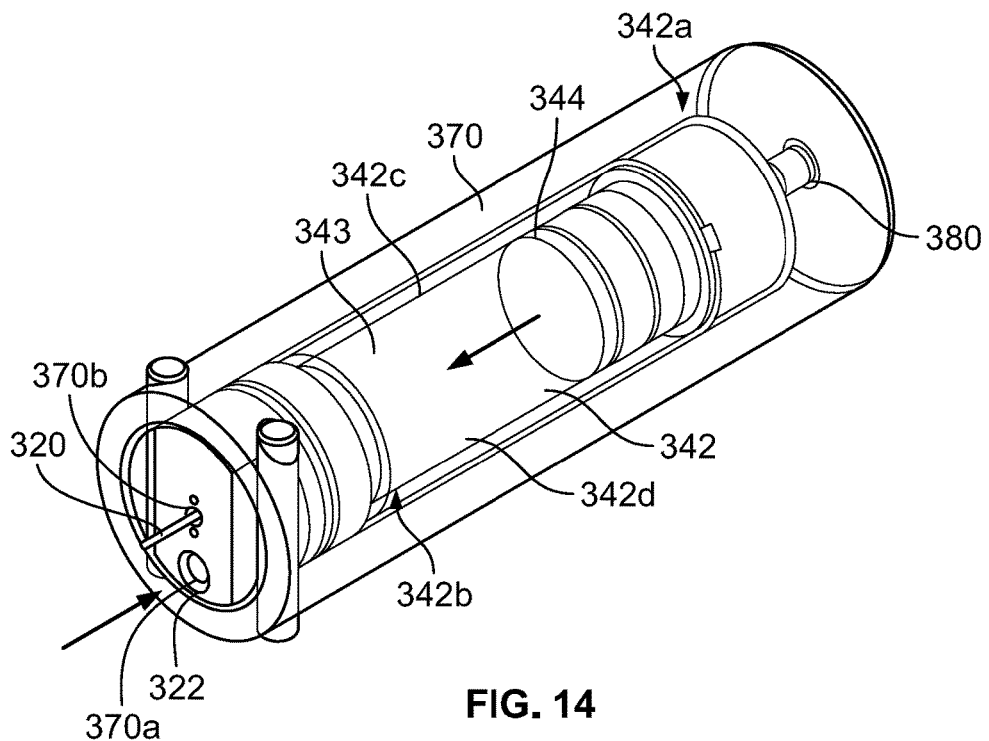
FIG. 14 illustrates an example drug delivery process of the pressure drive system of FIGS. 11-13b in accordance with various embodiments.

As illustrated in FIG. 14, the pressure chamber 370 includes a first opening 370a that accommodates the third connection 322. This opening allows the compressed gas 353a to enter the pressure chamber and surround the container 342. The compressed gas 353a then advances towards a first end 342a of the container 342 and begins to urge the plunger 344 forward towards the second end 342b of the container 342. This urging by the plunger 344 causes the medicament 343 to flow through the second connection 320 disposed in a second opening 370b and back to the cannula insertion mechanism 310 as illustrated in FIG. 13b. Accordingly, the medicament 343 is delivered to the user via the needle or cannula 312.

It is noted that the compressed gas 353a exerts an equalizing force on an outer surface 342c of the container 342 that opposes a force exerted on an inner surface 342d by the plunger 344 advancing the medicament 343. Accordingly, the container 342 does not experience substantial stresses that may be potentially damaging to the system 300.

Figure 15A:
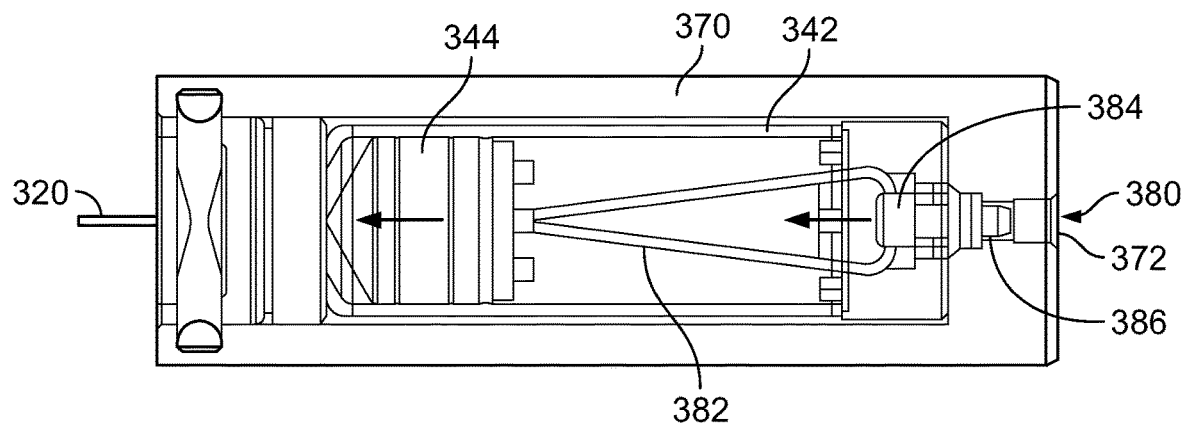
FIGS. 15a and 15b illustrate an example pressure relief process of the pressure drive system of FIGS. 11-14 in accordance with various embodiments.
Figure 15B:
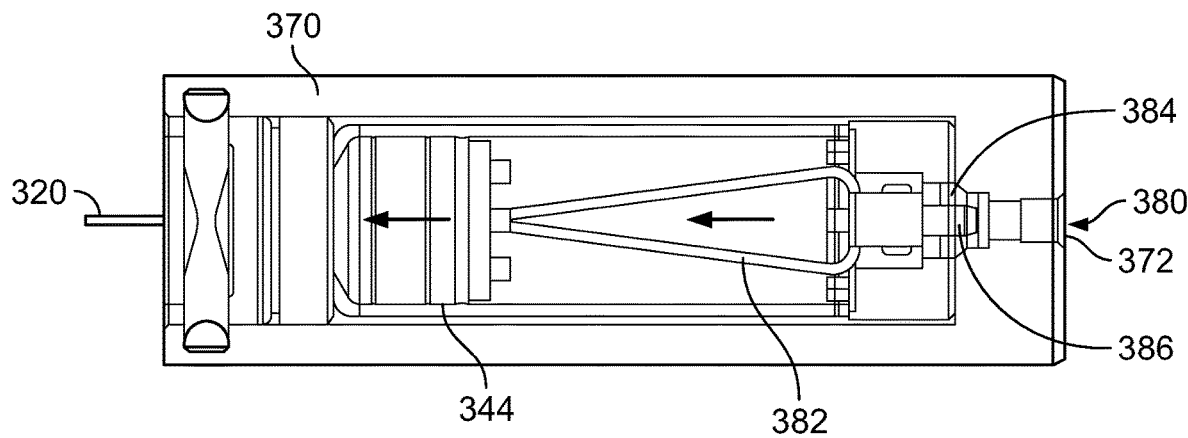
Figure 16:
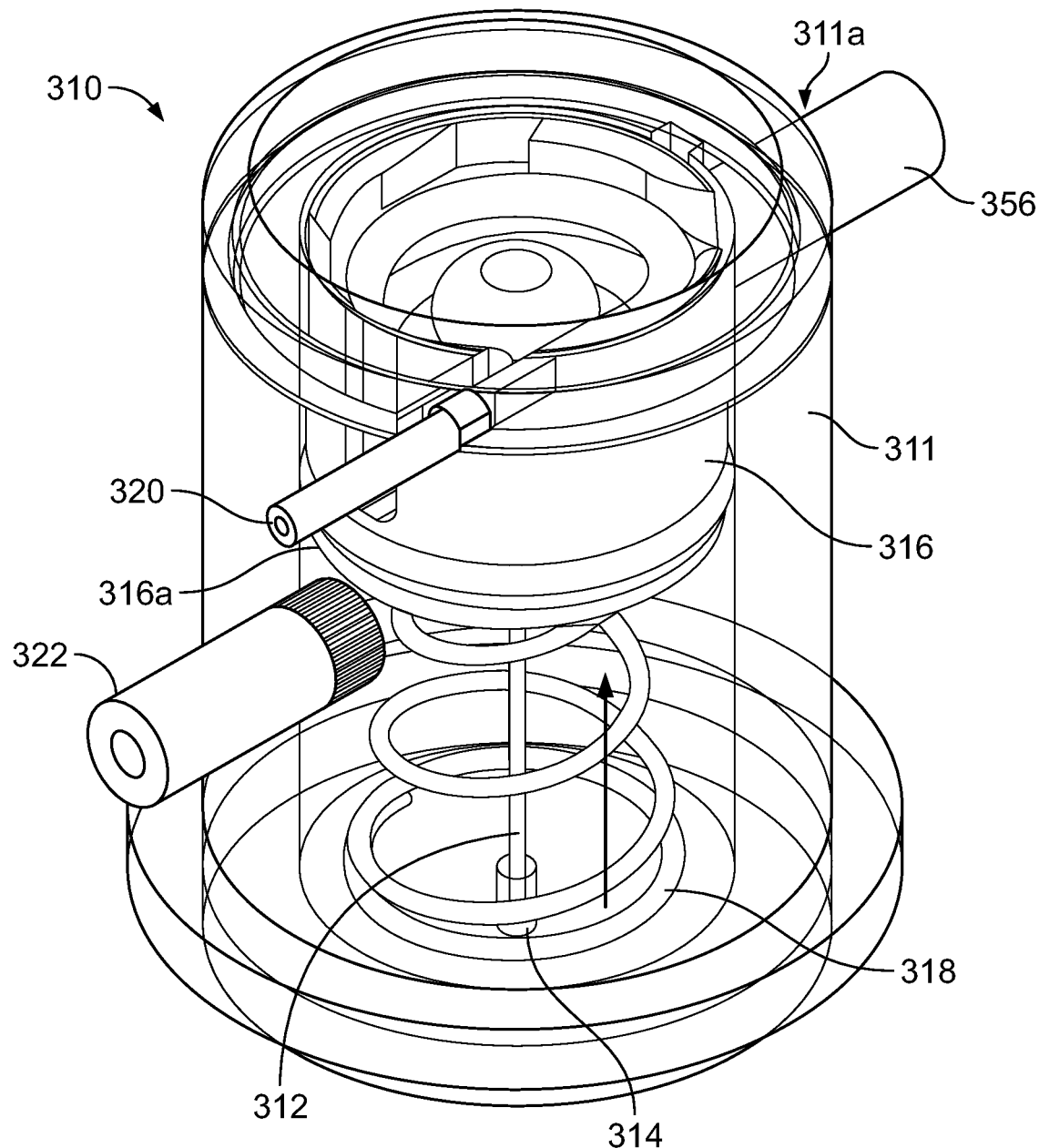
FIG. 16 illustrates an example cannula retraction process of the pressure drive system of FIGS. 11-15b in accordance with various embodiments.

As illustrated in FIGS. 15a and 15b, a relief mechanism 380 is provided in the pressure chamber 370. As illustrated in FIG. 15a, as the plunger 344 nears the second end 342b of the container 342, thereby signifying near-completion of delivery of the medicament 343, a cable 382 coupled to the plunger 344 becomes tensioned. The cable 382 is coupled to a release 384 having a plug 386 that is disposed in a relief opening 372 of the pressure chamber 370. As illustrated in FIG. 15b, when the plunger 344 reaches its end of travel, tension on the cable 382 causes the pressure relief mechanism 380 to be activated. The plug 386 is suitably displaced from the relief opening 372 to allow pressure from the compressed gas 353a to be relieved through the relief opening 372. Accordingly, as illustrated in FIG. 16, the resilient member 318 of the cannula insertion mechanism 310 urges the sliding plunger assembly 316 upwards, thereby removing or retracting the needle or cannula 312 from the user. In some examples, the relief opening 372 may also include a flow restriction element such as a porous filter. This element may act as a "muffler" that reduces the noise of the venting gas. Additionally this element may assist in slowing down pressure decay, thus ensuring that all of the medicament is delivered to the user.

Figure 17A:
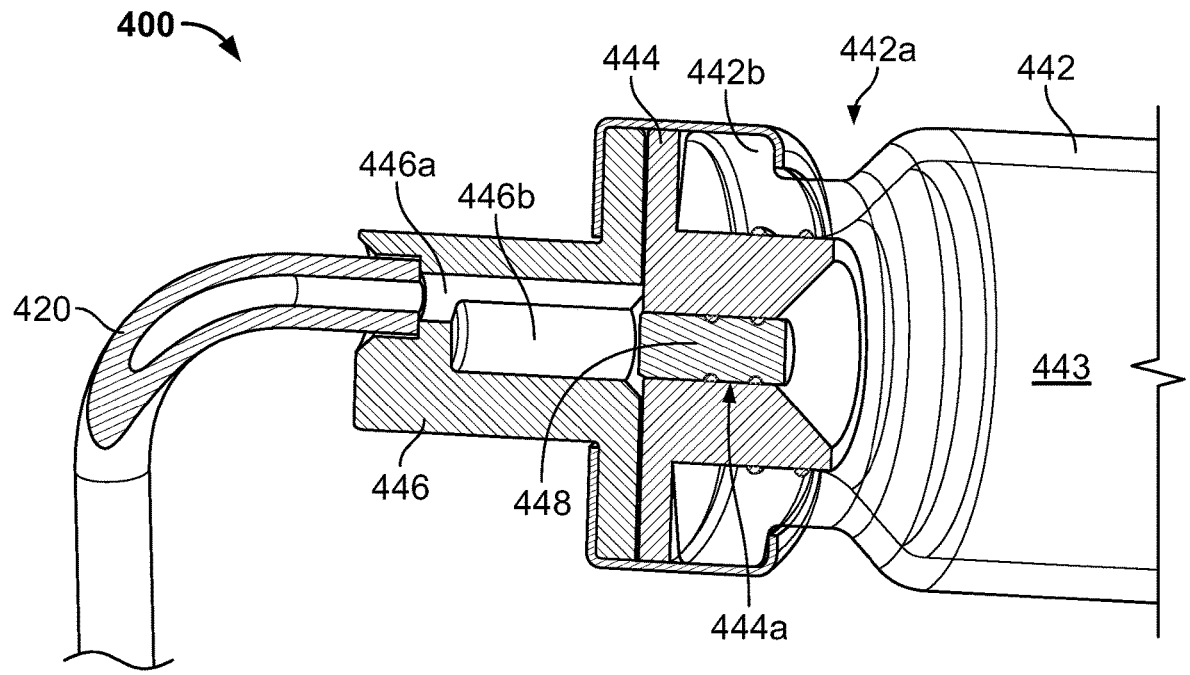
FIGS. 17a and 17b illustrate an alternate arrangement where a movable plug is urged away from a stopper to allow medicament to be distributed in accordance with various embodiments.
Figure 17B:
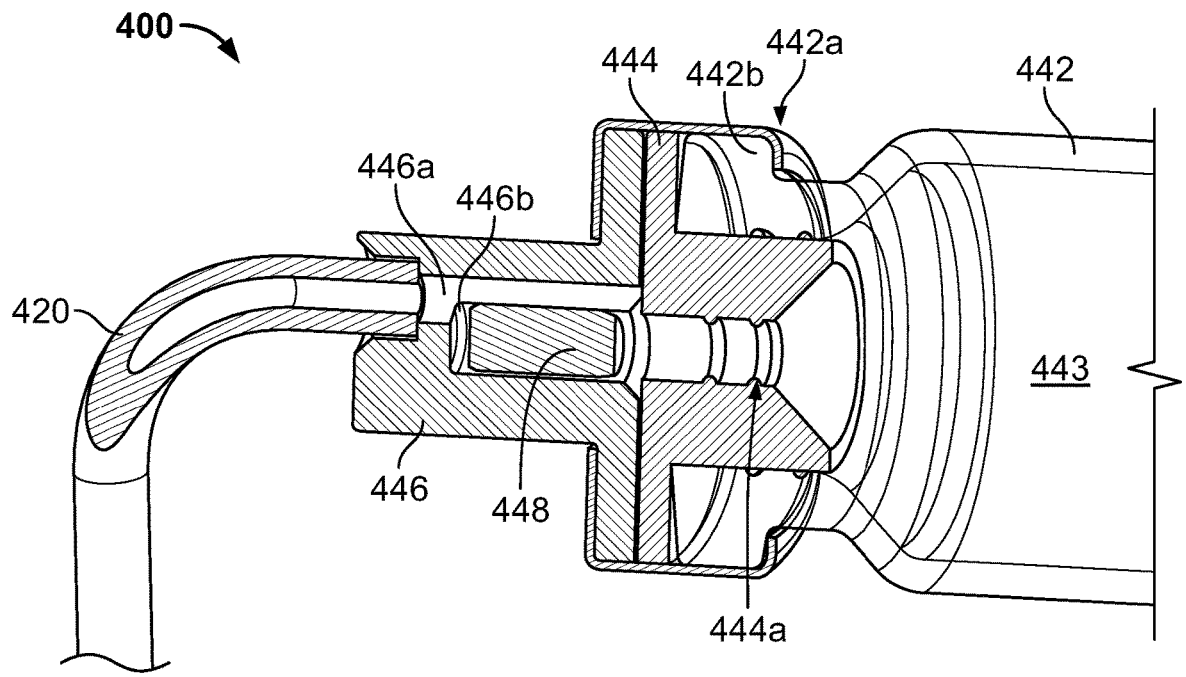

The foregoing description provides several approaches to piercing the primary container containing the medicament. In other approaches, pressure may urge a stopper out of an end of the vial, thereby exposing the fluid flow path. As illustrated in FIGS. 17a and 17b, a system 400 may include similar features and elements as the drug delivery devices and systems 100, 200, 200', 200", and 300, and thus have reference numerals with identical two-digit suffixes as those in the drug delivery devices of FIGS. 2-16. As such, for the sake of brevity, similar components will not be described in detail. The system 400 may include additional components not illustrated in the Figures. A first end 442a of a container 442 containing medicament 443 may include a volume 442b to accommodate an elastomeric stopper 444 having an inner bore 444a. A manifold cap 446 is positioned adjacent to the elastomeric stopper 444, and includes a bore 446a to accommodate a connection 420 that allows medicament to flow. The manifold cap 446 further includes a volume 446b in fluid connection with the bore 446a. As illustrated in FIG. 17a, a movable pin 448 is initially disposed in the inner bore 444a and acts as a plug to restrict medicament flow through the connection 420. With reference to FIG. 17b, during delivery, fluid pressure urges the movable pin 448 into the volume 446b. Accordingly, medicament 442 may flow from the inner bore 444a of the elastomeric stopper and through the manifold cap 446.

Figure 18A:
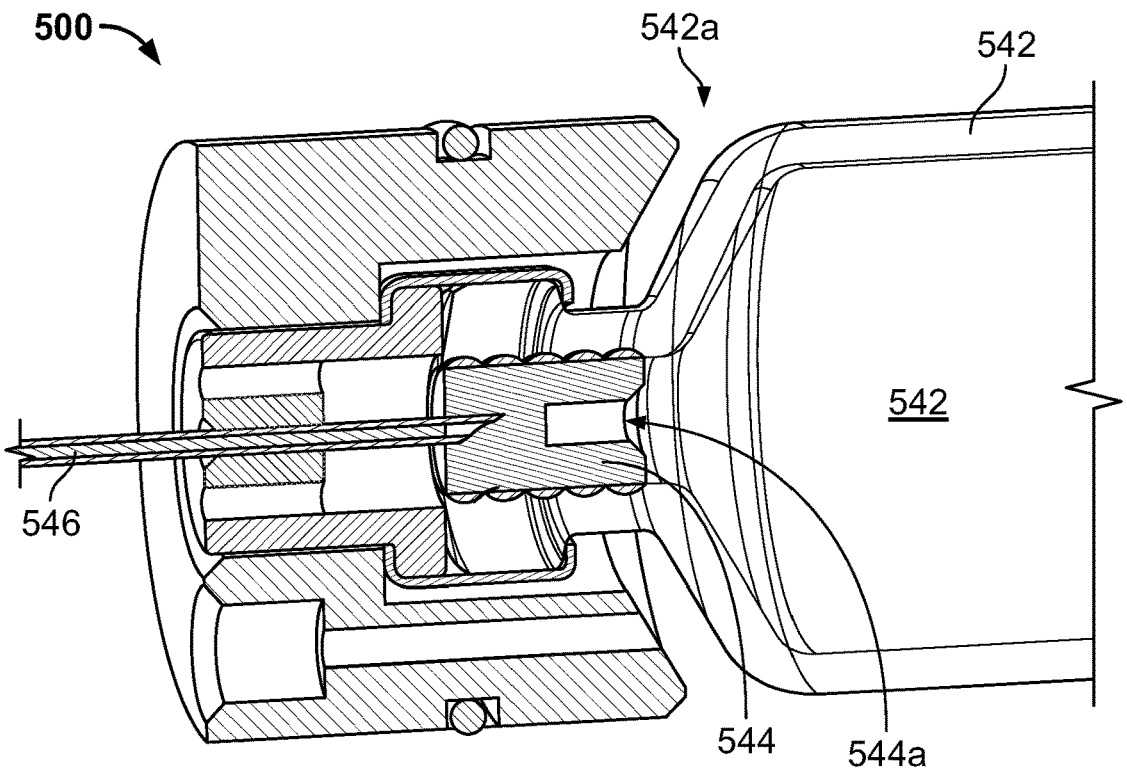
FIGS. 18a and 18b illustrate an alternate arrangement where a movable plug is pierced by a spike to allow medicament to be distributed in accordance with various embodiments.
Figure 18B:
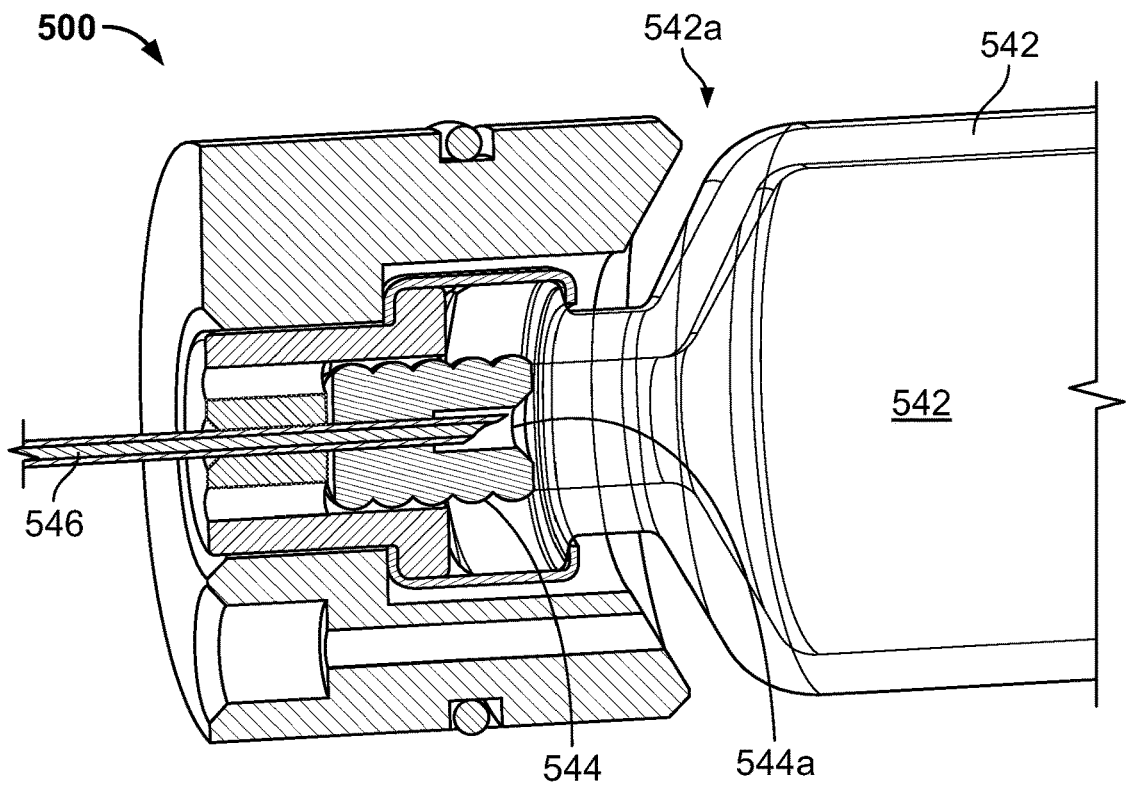

In some of these examples, the stopper may contact a fixed spike to expose the fluid flow path upon being urged out of the end of the vial. As illustrated in FIGS. 18a and 18b, a system 500 may include similar features and elements as the drug delivery devices and systems 100, 200, 200', 200", 300, and 400, and thus have reference numerals with identical two-digit suffixes as those in the drug delivery devices of FIGS. 2-17b. As such, for the sake of brevity, similar components will not be described in detail. The system 500 may include additional components not illustrated in the Figures. A first end 542a of a container 542 containing medicament 543 may be temporarily sealed by a movable elastomeric stopper 544 (FIG. 18a). The elastomeric stopper may include a bore 544a at one end and may have an embedded spike 546 disposed at an opposite end. The system 500 further includes a manifold 548 that surrounds the spike 546 and includes a volume 548a. As illustrated in FIG. 18b, during delivery, fluid pressure urges the elastomeric stopper 544 into the volume 548a, which causes the spike 546 to further pierce the elastomeric stopper 544 such that the spike 546 enters the bore 544a. As such, medicament 542 may flow from the bore 544a and though the spike 546.

While the foregoing description provides multiple different "embodiments" for the type of actuating mechanisms that may be incorporated into the systems disclosed herein, it should be appreciated that the different actuating mechanisms and pressure chambers could also be combined with each other, as desired. That is, a person of ordinary skill would understand that a pressure chamber (e.g., FIGS. 5a-16) could be combined with a pneumatic actuating mechanism disclosed herein (e.g., FIGS. 2-4b).

Figure 19A:
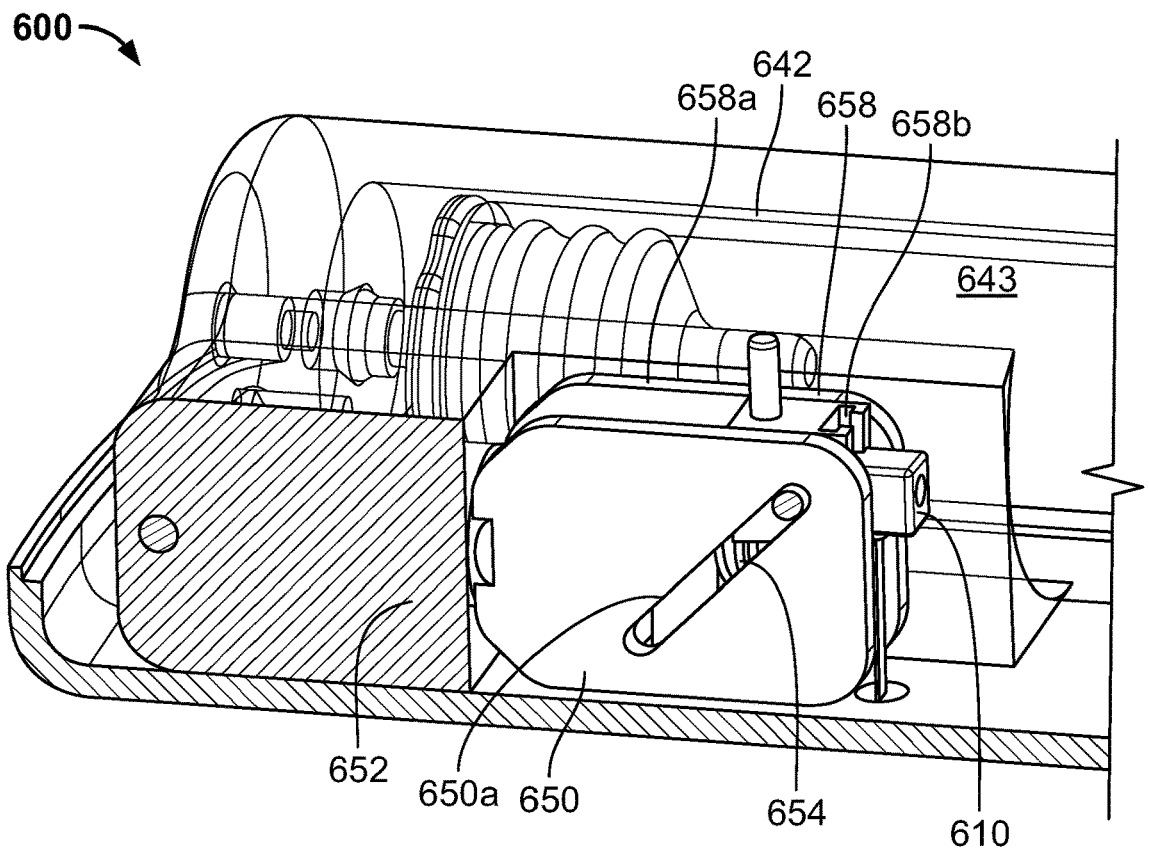
FIGS. 19a and 19b illustrate an alternate arrangement having an indirect insertion mechanism coupling in accordance with various embodiments.
Figure 19B:
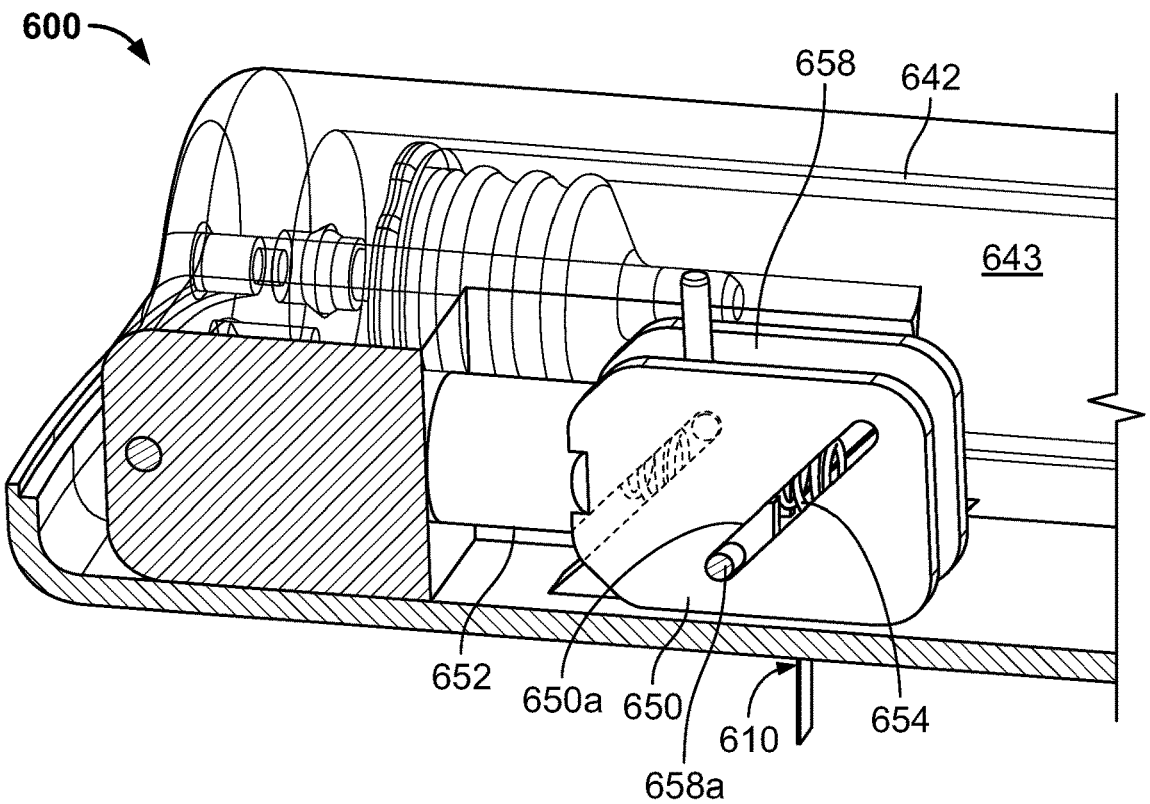

As illustrated in FIGS. 19a and 19b, a system 600 may include similar features and elements as the drug delivery devices and systems 100, 200, 200', 200", 300, 400, and 500, and thus have reference numerals with identical two-digit suffixes as those in the drug delivery devices of FIGS. 2-18b. As such, for the sake of brevity, similar components will not be described in detail. The system 600 may include additional components not illustrated in the Figures. In the system 600, the needle insertion/retraction process, also known as cannulation, is achieved via a hydraulic and/or pneumatic needle insertion/retraction module 650. In some examples, the module 650 may be directly coupled with the cannula connected to a piston, or alternatively, may be indirectly coupled through the illustrated mechanism. The module 650 is pressurized at the same time as the primary container 642 by the same gas driving a stopper in the primary container 642 and has a movable piston 652 at a proximal end connected to a spring 654 at a distal end. The piston 652 moves forward when module is pressurized and compresses the spring 654 at distal end. The piston 652 likewise is connected to a cam mechanism 658 containing the needle hub or assembly 610 as a follower. As the piston 652 moves, the needle hub 610 is driven downwards via the cam mechanism 658 to penetrate the skin. Specifically, the cam mechanism 658 includes a shaft 658a that is inserted into a slot 650a of the module 650. Further, the needle hub 610 is slidably disposed in a channel 658b of the cam mechanism 658 via a protrusion (not illustrated) that corresponds to the shape of the channel 658b. As illustrated in FIG. 19a, in a first position, the cam mechanism 658 is in a first configuration where the needle hub 610 is not inserted into the skin. In FIG. 19b, the piston 652 moves forward, and advances the module 650 relative to the cam mechanism 658. Accordingly, the shaft 658a advances downwards through the slot, which in turn causes the needle hub 610 to move downwards in the channel 658b to be inserted into the skin.

At the onset of pressurization of the primary drug container, a movable septa-plug in the distal end of the primary container is moved forward to be penetrated by a fixed cannula at the distal end of the primary container. Once the cannula penetrates the plug-septa assembly, the fluidic path from the primary drug container to the skin is established. This process is fairly rapid, but it ensures a delay before the fluidic path is established to allow for the needle in the needle insertion/retraction module to penetrate the skin first. The cannula stays in the skin until pressure drops in the needle insertion/retraction or cannulation module.

In some examples, the pressure may drop when the stopper in the primary drug container reaches the end of travel. This may occur when all drug contents have been delivered to the patient and stopper reached the neck area of the primary drug container. At this point, the chamber pressure drops via a pressure relief plug at proximal end of the primary drug container. As the stopper in the primary drug container moves forward, a plug at proximal end of the pressure chamber that is tethered to the stopper by a Kevlar string or similarly known material to art is pulled to open a relief valve to relieve any residual gas pressure in drive mechanism. The drop in pressure also allows for the previously compressed spring 654 at the distal end of the pneumatic needle insertion/retraction module 650 to relax and push the piston 652 back, thereby resulting in the needle being retracted from the skin. By tuning the pressure drop rate profile, the speed of needle retraction can be tuned. The retraction speed is also affected by the friction of the piston and sliding elements such as a cam-follower assembly in the module.

Figure 20:
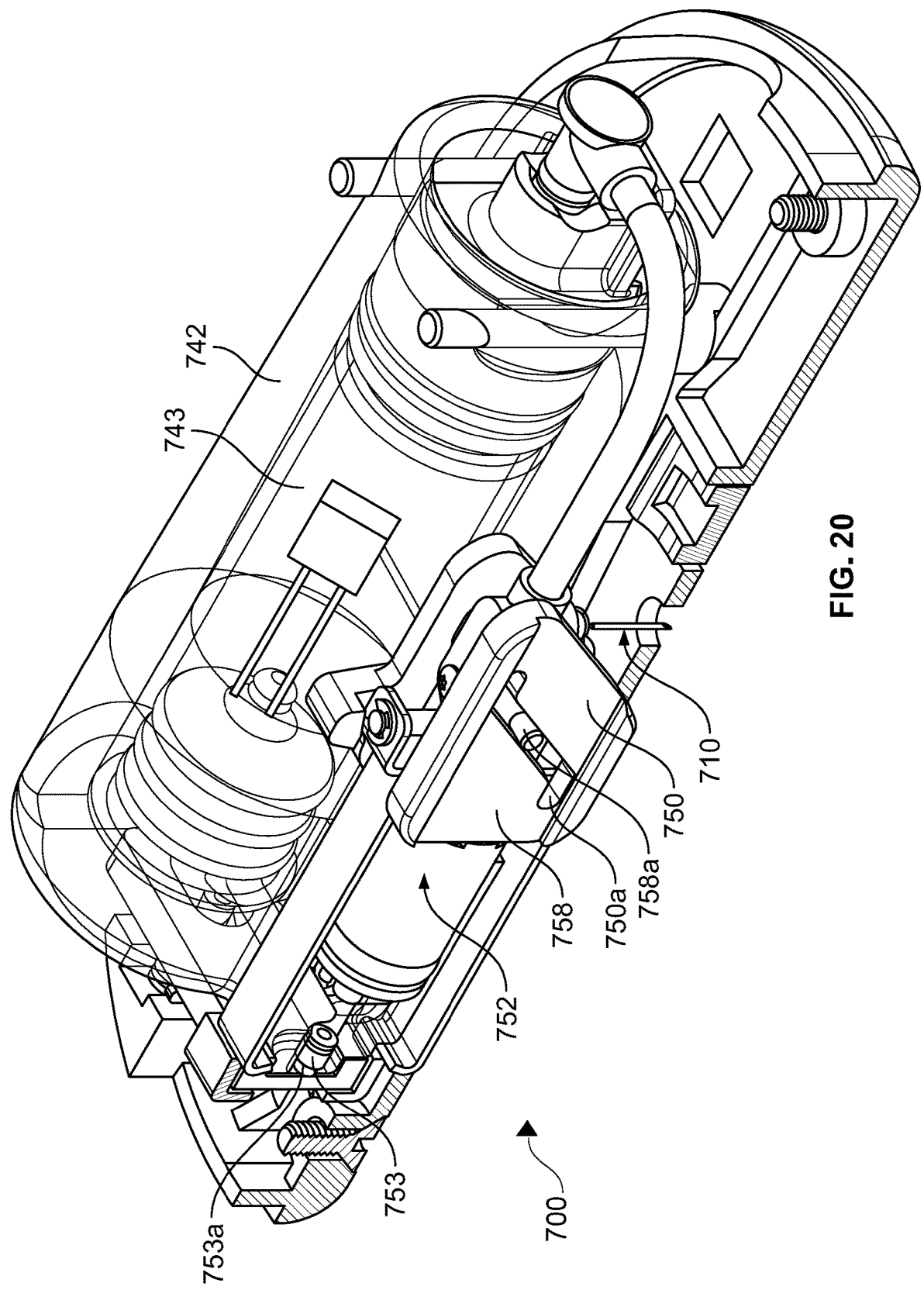
FIG. 20 illustrates a further alternate arrangement having an indirect insertion mechanism coupling in accordance with various embodiments.

As illustrated in FIG. 20, a system 700 may include similar features and elements as the drug delivery devices and systems 100, 200, 200', 200", 300, 400, 500, and 600, and thus have reference numerals with identical two-digit suffixes as those in the drug delivery devices of FIGS. 2-19b. As such, for the sake of brevity, similar components will not be described in detail. The system 700 may include additional components not illustrated in the Figures. In the system 700, which closely resembles the system 600, the needle insertion/retraction process is achieved via a hydraulic and/or pneumatic needle insertion/retraction module 750. In some examples, the module 750 may be directly coupled with the cannula connected to a piston, or alternatively, may be indirectly coupled through the illustrated mechanism. The module 750 is pressurized at substantially the same time as the primary container 742 by the same gas driving a stopper in the primary container 742 and has a movable piston 752 at a proximal end connected to a spring 754 at a distal end. The piston 752 includes a break-away protrusion 753 disposed at the proximal end to assist in the rapid release of gas for high speed needle or cannula insertion. The protrusion 753 includes one or more grooves 753a that form weak points, yet restrain the movement of the piston 752 until sufficient pressure has accumulated to break the protrusion 753. Upon the pressure increasing beyond the breakpoint, the needle is inserted much more rapidly. The protrusion 753 additionally partially blocks the gas path to the chamber with the drug vial to ensure that the needle hub 710 fires before drug delivery begins.

The piston 752 moves forward when module is sufficiently pressurized and compresses the spring 754 at the distal end. The piston 752 likewise is connected to a cam mechanism 758 containing the needle hub or assembly 710 as a follower. As the piston 752 moves, the needle hub 710 is driven downwards via the cam mechanism 758 to penetrate the skin. Specifically, the cam mechanism 758 includes a shaft 758a that is inserted into a slot 750a of the module 750.

At the onset of pressurization of the primary drug container, a movable septa-plug in the distal end of the primary container is moved forward to be penetrated by a fixed cannula at the distal end of the primary container. Once the cannula penetrates the plug-septa assembly, the fluidic path from the primary drug container to the skin is established. This process is fairly rapid due to the breakaway protrusion 753, which, as previously noted, also ensures a delay before the fluidic path is established to allow for the needle in the needle insertion/retraction module 710 to first penetrate the skin. The cannula remains in the skin until pressure drops in the needle insertion/retraction or cannulation module.

The above description describes various assemblies, devices, and methods for use with a drug delivery device. It should be clear that the assemblies, drug delivery devices, or methods can further comprise use of a medicament listed below with the caveat that the following list should neither be considered to be all inclusive nor limiting. The medicament will be contained in a reservoir. In some instances, the reservoir is a primary container that is either filled or pre-filled for treatment with the medicament. The primary container can be a cartridge or a pre-filled syringe.

For example, the drug delivery device or more specifically the reservoir of the device may be filled with colony stimulating factors, such as granulocyte colony-stimulating factor (G-CSF). Such G-CSF agents include, but are not limited to, Neupogen® (filgrastim) and Neulasta® (pegfilgrastim). In various other embodiments, the drug delivery device may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications, each of which is herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publication Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; U.S. Publication Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publication Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgastrim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publication No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of SEQ ID NO:2 as set forth therein in FIG. 2 and/or the heavy chain of SEQ ID NO:4, as set forth therein in FIG. 4, each of which is individually and specifically incorporated by reference herein in its entirety fully as disclosed in the foregoing publication;

Myostatin binding proteins, peptibodies, and related proteins, and the like, including myostatin specific peptibodies, particularly those described in U.S. Publication No. 2004/0181033 and PCT Publication No. WO 2004/058988, which are incorporated by reference herein in their entirety particularly in parts pertinent to myostatin specific peptibodies, including but not limited to peptibodies of the mTN8-19 family, including those of SEQ ID NOS:305-351, including TN8-19-1 through TN8-19-40, TN8-19 con1 and TN8-19 con2; peptibodies of the mL2 family of SEQ ID NOS:357-383; the mL15 family of SEQ ID NOS:384-409; the mL17 family of SEQ ID NOS:410-438; the mL20 family of SEQ ID NOS:439-446; the mL21 family of SEQ ID NOS:447-452; the mL24 family of SEQ ID NOS:453-454; and those of SEQ ID NOS:615-631, each of which is individually and specifically incorporated by reference herein in their entirety fully as disclosed in the foregoing publication;

IL-4 receptor specific antibodies, peptibodies, and related proteins, and the like, particularly those that inhibit activities mediated by binding of IL-4 and/or IL-13 to the receptor, including those described in PCT Publication No. WO 2005/047331 or PCT Application No. PCT/US2004/37242 and in U.S. Publication No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication;

Interleukin 1-receptor 1 ("IL1-R1") specific antibodies, peptibodies, and related proteins, and the like, including but not limited to those described in U.S. Publication No. 2004/097712, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned publication;

Ang2 specific antibodies, peptibodies, and related proteins, and the like, including but not limited to those described in PCT Publication No. WO 03/057134 and U.S. Publication No. 2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2xL1(N); 2xL1(N) WT; Con4 (N), Con4 (N) 1K WT, 2xCon4 (N) 1K; L1C; L1C 1 K; 2xL1C; Con4C; Con4C 1 K; 2xCon4C 1K; Con4-L1 (N); Con4-L1C; TN-12-9 (N); C17 (N); TN8-8(N); TN8-14 (N); Con 1 (N), also including anti-Ang 2 antibodies and formulations such as those described in PCT Publication No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; AbIA1; AbIF; AbIK; AbIP; and AbIP, in their various permutations as described therein, each of which is individually and specifically incorporated by reference herein in its entirety fully as disclosed in the foregoing publication;

NGF specific antibodies, peptibodies, and related proteins, and the like including, in particular, but not limited to those described in U.S. Publication No. 2005/0074821 and U.S. Pat. No. 6,919,426, which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication;

CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but not limited to, for example, the human CD22 specific fully humanized antibody in Epratuzumab, CAS registry number 501423-23-0;

IGF-1 receptor specific antibodies, peptibodies, and related proteins, and the like, such as those described in PCT Publication No. WO 06/069202, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing publication;

Also among non-limiting examples of anti-IGF-1R antibodies for use in the methods and compositions of the present invention are each and all of those described in:

(i) U.S. Publication No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publication No. WO 06/138729 (published Dec. 28, 2006) and WO 05/016970 (published Feb. 24, 2005), and Lu et al. (2004), J. Biol. Chem. 279:2856-2865, including but not limited to antibodies 2F8, A12, and IMC-A12 as described therein;

(iii) PCT Publication No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

(iv) U.S. Publication No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

(v) U.S. Publication Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al. (2003), Cancer Res. 63:5073-5083, including but not limited to antibody EM164, resurfaced EM164, humanized EM164, huEM164 v1.0, huEM164 v1.1, huEM164 v1.2, and huEM164 v1.3 as described therein;

(vi) U.S. Pat. No. 7,037,498 (issued May 2, 2006), U.S. Publication Nos. 2005/0244408 (published Nov. 30, 2005) and 2004/0086503 (published May 6, 2004), and Cohen, et al. (2005), Clinical Cancer Res. 11:2063-2073, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) U.S. Publication Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA (γ4), deposited at the ATCC under number PTA-5214, and a light chain encoded by a polynucleotide in plasmid 15H12/19D12 LCF (κ), deposited at the ATCC under number PTA-5220, as described therein; and (viii) U.S. Publication No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publication No. 2008/0166352 and PCT Publication No. WO 07/011941, which are incorporated herein by reference in their entireties as to such antibodies and related proteins, including but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO:9 respectively therein); 2H (having light chain variable and heavy chain variable sequences SEQ ID NO:3 and SEQ ID NO:10 respectively therein); 43H (having light chain variable and heavy chain variable sequences SEQ ID NO:6 and SEQ ID NO:14 respectively therein); 41H (having light chain variable and heavy chain variable sequences SEQ ID NO:5 and SEQ ID NO:13 respectively therein); and 15H (having light chain variable and heavy chain variable sequences SEQ ID NO:4 and SEQ ID NO:12 respectively therein), each of which is individually and specifically incorporated by reference herein in its entirety fully as disclosed in the foregoing publication;

IL-15 specific antibodies, peptibodies, and related proteins, and the like, such as, in particular, humanized monoclonal antibodies, particularly antibodies such as those disclosed in U.S. Publication Nos. 2003/0138421; 2003/023586; and 2004/0071702; and U.S. Pat. No. 7,153,507, each of which is incorporated herein by reference in its entirety as to IL-15 specific antibodies and related proteins, including peptibodies, including particularly, for instance, but not limited to, HuMax IL-15 antibodies and related proteins, such as, for instance, 146B7;

IFN gamma specific antibodies, peptibodies, and related proteins and the like, especially human IFN gamma specific antibodies, particularly fully human anti-IFN gamma antibodies, such as, for instance, those described in U.S. Publication No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing publication and in Thakur et al. (1999), Mol. Immunol. 36:1107-1115. In addition, description of the properties of these antibodies provided in the foregoing publication is also incorporated by reference herein in its entirety. Specific antibodies include those having the heavy chain of SEQ ID NO:17 and the light chain of SEQ ID NO:18; those having the heavy chain variable region of SEQ ID NO:6 and the light chain variable region of SEQ ID NO:8; those having the heavy chain of SEQ ID NO:19 and the light chain of SEQ ID NO:20; those having the heavy chain variable region of SEQ ID NO:10 and the light chain variable region of SEQ ID NO:12; those having the heavy chain of SEQ ID NO:32 and the light chain of SEQ ID NO:20; those having the heavy chain variable region of SEQ ID NO:30 and the light chain variable region of SEQ ID NO:12; those having the heavy chain sequence of SEQ ID NO:21 and the light chain sequence of SEQ ID NO:22; those having the heavy chain variable region of SEQ ID NO:14 and the light chain variable region of SEQ ID NO:16; those having the heavy chain of SEQ ID NO:21 and the light chain of SEQ ID NO:33; and those having the heavy chain variable region of SEQ ID NO:14 and the light chain variable region of SEQ ID NO:31, as disclosed in the foregoing publication. A specific antibody contemplated is antibody 1119 as disclosed in the foregoing U.S. publication and having a complete heavy chain of SEQ ID NO:17 as disclosed therein and having a complete light chain of SEQ ID NO:18 as disclosed therein;

TALL-1 specific antibodies, peptibodies, and the related proteins, and the like, and other TALL specific binding proteins, such as those described in U.S. Publication Nos. 2003/0195156 and 2006/0135431, each of which is incorporated herein by reference in its entirety as to TALL-1 binding proteins, particularly the molecules of Tables 4 and 5B, each of which is individually and specifically incorporated by reference herein in its entirety fully as disclosed in the foregoing publications;

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH;

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in U.S. Publication No. 2005/0118643 and PCT Publication No. WO 2005/017107, huL2G7 described in U.S. Pat. No. 7,220,410 and OA-5d5 described in U.S. Pat. Nos. 5,686,292 and 6,468,529 and in PCT Publication No. WO 96/38557, each of which is incorporated herein by reference in its entirety, particularly in parts pertinent to proteins that bind HGF;

TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2;

Activin A specific antibodies, peptibodies, related proteins, and the like, including but not limited to those described in U.S. Publication No. 2009/0234106, which is herein incorporated by reference in its entirety, particularly in parts pertinent to proteins that bind Activin A;

TGF-beta specific antibodies, peptibodies, related proteins, and the like, including but not limited to those described in U.S. Pat. No. 6,803,453 and U.S. Publication No. 2007/0110747, each of which is herein incorporated by reference in its entirety, particularly in parts pertinent to proteins that bind TGF-beta;

Amyloid-beta protein specific antibodies, peptibodies, related proteins, and the like, including but not limited to those described in PCT Publication No. WO 2006/081171, which is herein incorporated by reference in its entirety, particularly in parts pertinent to proteins that bind amyloid-beta proteins. One antibody contemplated is an antibody having a heavy chain variable region comprising SEQ ID NO:8 and a light chain variable region having SEQ ID NO:6 as disclosed in the foregoing publication;

c-Kit specific antibodies, peptibodies, related proteins, and the like, including but not limited to those described in U.S. Publication No. 2007/0253951, which is incorporated herein by reference in its entirety, particularly in parts pertinent to proteins that bind c-Kit and/or other stem cell factor receptors;

OX40L specific antibodies, peptibodies, related proteins, and the like, including but not limited to those described in U.S. Publication No. 2006/0002929, which is incorporated herein by reference in its entirety, particularly in parts pertinent to proteins that bind OX40L and/or other ligands of the OX40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4β7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgastrim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIIa receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507); Tysabri® (natalizumab, anti-α4integrin mAb); Valortim® (MDX-1303, anti-*B. anthracis* protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Rα mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab), as well as molecules, variants, analogs or derivatives thereof as disclosed in the following patents or patent applications, each of which is herein incorporated by reference in its entirety for all purposes: U.S. Pat. No. 8,030,547, U.S. Publication No. 2013/0064825, WO2008/057457, WO2008/057458, WO2008/057459, WO2008/063382, WO2008/133647, WO2009/100297, WO2009/100318, WO2011/037791, WO2011/053759, WO2011/053783, WO2008/125623, WO2011/072263, WO2009/055783, WO2012/0544438, WO2010/029513, WO2011/111007, WO2010/077854, WO2012/088313, WO2012/101251, WO2012/101252, WO2012/101253, WO2012/109530, and WO2001/031007.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223, 593 and 7,537,924); OncoVEXGALV/CD (U.S. Pat. No. 7,981,669); OrienX010 (Lei et al. (2013), World J. Gastroenterol., 19:5138-5143); G207, 1716; NV1020; NV12023; NV1034 and NV1042 (Vargehes et al. (2002), Cancer Gene Ther., 9(12):967-978).

Also included are TIMPs. TIMPs are endogenous tissue inhibitors of metalloproteinases (TIMPs) and are important in many natural processes. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003, the disclosure of which is incorporated by reference herein. Description of TIMP mutations can be found in U.S. Publication No. 2014/0274874 and PCT Publication No. WO 2014/152012.

Also included are antagonistic antibodies for human calcitonin gene-related peptide (CGRP) receptor and bispecific antibody molecule that target the CGRP receptor and other headache targets. Further information concerning these molecules can be found in PCT Application No. WO 2010/075238.

Additionally, bispecific T cell engager (BiTE®) antibodies, e.g. BLINCYTO® (blinatumomab), can be used in the device. Alternatively, included can be an APJ large molecule agonist e.g., apelin or analogues thereof in the device. Information relating to such molecules can be found in PCT Publication No. WO 2014/099984.

In certain embodiments, the medicament comprises a therapeutically effective amount of an anti-thymic stromal lymphopoietin (TSLP) or TSLP receptor antibody. Examples of anti-TSLP antibodies that may be used in such embodiments include, but are not limited to, those described in U.S. Pat. Nos. 7,982,016, and 8,232,372, and U.S. Publication No. 2009/0186022. Examples of anti-TSLP receptor antibodies include, but are not limited to, those described in U.S. Pat. No. 8,101,182. In particularly preferred embodiments, the medicament comprises a therapeutically effective amount of the anti-TSLP antibody designated as A5 within U.S. Pat. No. 7,982,016.

Although the drug delivery devices, methods, and components thereof, have been described in terms of exemplary embodiments, they are not limited thereto. The detailed description is to be construed as exemplary only and does not describe every possible embodiment of the invention because describing every possible embodiment would be impractical, if not impossible. Numerous alternative embodiments could be implemented, using either current technology or technology developed after the filing date of this patent that would still fall within the scope of the claims defining the invention. For example, components described herein with reference to certain kinds of drug delivery devices, such as on-body injector drug delivery devices or other kinds of drug delivery devices, can also be utilized in other kinds of drug delivery devices, such as autoinjector drug delivery devices.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

The patent claims at the end of this patent application are not intended to be construed under 35 U.S.C. § 112(f) unless traditional means-plus-function language is expressly recited, such as "means for" or "step for" language being explicitly recited in the claim(s). The systems and methods described herein are directed to an improvement to computer functionality, and improve the functioning of conventional computers.

What is claimed is:

1. A wearable drug delivery device comprising:
a housing defining a shell;
a needle assembly at least partially disposed within the housing, the needle assembly comprising a 1) needle or a cannula; and 2) a sterile barrier disposed proximal to the needle or cannula in a first configuration where the sterile barrier is intact;
a drive assembly at least partially disposed within the housing and operably coupled to the needle assembly, the drive assembly comprising:
a container having a first end, a second end, an inner surface, and an outer surface, an inner volume of the container being adapted to contain a medicament to be administered to a user, the sterile barrier being positioned at the second end of the container;
a first plunger being disposed in the first end of the container, the first plunger and the inner surface of the container cooperating to initially encapsulate the medicament within the container;
a second plunger positioned within the inner volume of the container near the second end thereof, the needle or cannula being coupled with the second plunger, wherein the second plunger cooperates with the container to define a void at the second end thereof; and
a drive mechanism adapted to be actuated to exert a force on the first plunger to urge the medicament through the container, the drive mechanism including a hydraulic fluid or a pressurized gas disposed within a separate drive container fluidly coupled with the first end of the container via a drive connection comprising a tube, and an urging component disposed at the first end of the container, the urging component comprising an elastic member adapted to receive a volume of the hydraulic fluid or the pressurized gas therein;
wherein upon actuating the drive mechanism, the hydraulic fluid or pressurized gas of the drive mechanism enters the container and a portion of the elastic member, thereby causing the elastic member to inflate and exert the force on the first plunger, whereupon the medicament initially encapsulated within the inner volume of the container defined by the inner surface thereof and the first plunger exerts a force that moves the second plunger and the needle or cannula towards the sterile barrier from the first configuration to a second configuration where the needle or cannula breaks the sterile barrier, thereby allowing the medicament to be administered via the needle or cannula.

2. The wearable drug delivery device of claim 1, wherein the drive assembly further comprises an outer shell that at least partially surrounds the container to define a pressure equalizing chamber therebetween, wherein the drive mechanism is further adapted to exert an equalizing pressure on the outer surface of the container that is approximately equal to the force exerted on the first plunger.

3. The wearable drug delivery device of claim 1, wherein the drive mechanism further comprises at least one of (a) and (b):
 (a) a pressurized gas cartridge that, when engaged, releases the pressurized gas that exerts a force on the first plunger,
 (b) a resilient member adapted to urge the hydraulic fluid towards the first plunger.

4. The wearable drug delivery device of claim 1, wherein the sterile barrier is
 disposed on the second plunger positioned near the second end of the container, the second plunger being adapted to be urged by the medicament towards the second end of the container, thereby moving the needle or cannula and the sterile barrier to the second configuration to break the sterile barrier.

5. The wearable drug delivery device of claim 1, further comprising at least one of (a) and (b):
 (a) a release mechanism operably coupled to the first plunger to at least partially relieve the first plunger from being urged towards the second end of the container,
 (b) a medicament disposed in the container to be administered to the user.

* * * * *

UNITED STATES PATENT AND TRADEMARK OFFICE
CERTIFICATE OF CORRECTION

| | | |
|---|---|---|
| PATENT NO. | : 12,318,593 B2 | Page 1 of 1 |
| APPLICATION NO. | : 16/630329 | |
| DATED | : June 3, 2025 | |
| INVENTOR(S) | : Mehran Mojarrad et al. | |

It is certified that error appears in the above-identified patent and that said Letters Patent is hereby corrected as shown below:

On the Title Page

At Item (72), Line 2, "John K. Hoffman," should be -- John K. Hoffman, Deceased, --.

Signed and Sealed this
Eighteenth Day of November, 2025

John A. Squires
*Director of the United States Patent and Trademark Office*